United States Patent [19]

Porter et al.

[11] Patent Number: 5,637,593
[45] Date of Patent: Jun. 10, 1997

[54] TRYPTAMINE ANALOGUES AS 5-HT1-LIKE AGONISTS

[75] Inventors: Roderick A. Porter, Ashwell; John G. Ward, Barnet, both of England

[73] Assignee: SmithKline Beecham plc, England

[21] Appl. No.: 448,544

[22] PCT Filed: Dec. 14, 1993

[86] PCT No.: PCT/EP93/03563

§ 371 Date: Jun. 20, 1995

§ 102(e) Date: Jun. 20, 1995

[87] PCT Pub. No.: WO94/14770

PCT Pub. Date: Jul. 7, 1994

[30] Foreign Application Priority Data

Dec. 21, 1992 [GB] United Kingdom ............... 9226532

[51] Int. Cl.$^6$ .......................... A61K 31/40; C07D 401/12
[52] U.S. Cl. .................. 514/274; 514/318; 514/339; 514/415; 544/310; 544/316; 546/193; 546/194; 546/201; 548/504; 548/505
[58] Field of Search ................... 514/274, 318, 514/339, 415; 544/310, 316; 546/193, 194, 201; 548/504, 505

[56] References Cited

U.S. PATENT DOCUMENTS

| 5,245,046 | 9/1993 | Youngdale et al. ............ 548/495 |
| 5,401,854 | 3/1995 | Haffer et al. ................. 548/469 |

FOREIGN PATENT DOCUMENTS

| 0505322 | 9/1992 | European Pat. Off. . |
| 91/18897 | 12/1991 | WIPO . |
| 92/13856 | 8/1992 | WIPO . |
| 93/00333 | 1/1993 | WIPO . |
| 93/11106 | 6/1993 | WIPO . |

OTHER PUBLICATIONS

Chem Abs, vol. 106, No. 13, 30 Mar. 1987, 98661w, Mukhomorov V.K. 'Influence of electronic and steric interactions on the radioprotective properties of indolylalkylamines'.

J. Med. Chem. vol. 36, No. 11, 28 May 1993, pp. 1529–1538, L.J. Street et al. 'Synthesis and serotonergic activity of 5-(oxadiazolyl)tryptamines: potent agonists for 5-HT1D receptors'.

*Primary Examiner*—Jacqueline Haley
*Attorney, Agent, or Firm*—Nora Stein-Fernandez; William T. King; Edward T. Lentz

[57] ABSTRACT

A compound of structure (I), in which $A^1$ is O, $S(O)_n$ in which n is 0, 1 or 2, NR, $CH_2$, or CH(OH); $A^2$ is a bond or $CH_2$; or $A^1A^2$ is CH=CH; R is hydrogen or $C_{1-4}$alkyl; $R^1$ is an optionally substituted 6- to 10-membered aryl or heteroaryl ring; suitably $R^1$ is an optionally substituted 6-10-membered aryl ring such as phenyl or naphthyl; suitably $R^1$ is optionally substituted 6- to 10-membered heteroaryl ring, containing from 1 to 4 nitrogen atoms; $R^2$ is hydrogen, halogen, $C_{1-4}$alkyl, CN, $NO_2$ or $CF_3$; $R^3$ is $C(R^4)(R^5)$ $CH_2NR^6R^7$, —CH=NNHC(NH)$NH_2$ or a; $R^4$ and $R^5$ are independently hydrogen or $C_{1-4}$alkyl; $R^6$ and $R^7$ are the same or different and are each hydrogen or $C_{1-4}$alkyl or together with the nitrogen atom to which they are attached form a ring; $R^8$ is hydrogen, $C_{1-4}$alkyl, or $C_{3-6}$alkenyl; the dotted lines represent an optional bond; and q and m are independently 1 or 2; and pharmaceutically acceptable salts, solvates and hydrates thereof. The compounds are 5-HT$_1$-like agonists (or partial agonists) and as such are expected to have utility in medicine in the treatment and/or prophylaxis of migraine, and other conditions associated with cephalic pain, such as cluster headache, headache associated with vascular disorders and other neuralgia. They are also expected to have utility in the treatment of prophylaxis of portal hypertension.

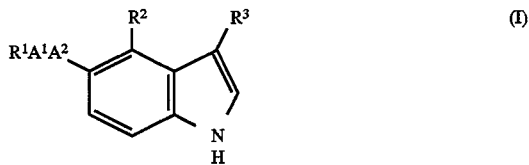

(I)

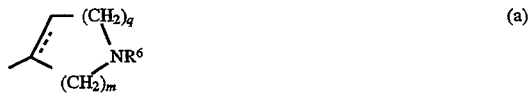

(a)

11 Claims, No Drawings

TRYPTAMINE ANALOGUES AS 5-HT1-LIKE AGONISTS

This application is a National Stage Application of PCT/EP93/03563 filed Dec. 14, 1993 which published as WO 94/14770 on Jul. 7, 1994.

The present invention relates to novel tryptamine analogues, processes and intermediates useful in their preparation, pharmaceutical compositions containing them and their use in therapy, in particular for the treatment and/or prophylaxis of disorders characterised by excessive vasodilatation, such as migraine and portal hypertension.

WO-A-93/11106 published after the priority date of the present application describes indole derivatives as serotonin (5HT$_1$) agonists. The generic disclosure of this document overlaps with the present application in describing compounds of structure (I) as hereinafter described wherein:
$R^1$ is a 6- to 10-membered aryl or heteroaryl ring optionally substituted by up to 3 groups selected from halo, $C_{1-4}$alkyl, $CO_2R^9$, NHCOR$^9$, CONR$^{10}$R$^{11}$, SO$_2$NR$^{10}$R$^{11}$, NHSO$_2$R$^{12}$, NO$_2$, NR$^{10}$R$^{11}$, NHCONH$_2$ or CN,
$A^1A^2$ is O, S or NH,
$R^2$ is hydrogen and
$R^3$ is (CH$_2$)$_2$NR$^6$R$^7$ or

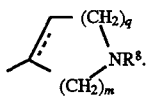

WO-A-93/11106 also specifically discloses as Example 1G a compound wherein $R^1$ is 3-CF$_3$-2-pyridyl, $A^1A^2$ is NH, $R^2$ is hydrogen and $R^3$ is CH$_2$CH$_2$NMe$_2$.

The present invention provides, in a first aspect, a compound of structure (I):

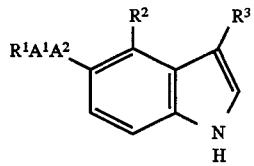

Structure (I)

in which
$A^1$ is O, S(O)$_n$ in which n is 0,1 or 2, NR, CH$_2$, or CH(OH);
$A^2$ is a bond or CH$_2$; or
$A^1A^2$ is CH=CH,
R is hydrogen or $C_{1-4}$alkyl,
$R^1$ is an optionally substituted 6- to 10-membered aryl or heteroaryl ring;
$R^2$ is hydrogen, halogen, $C_{1-4}$alkyl, CN, NO$_2$ or CF$_3$;
$R^3$ is C(R$^4$)(R$^5$)CH$_2$NR$^6$R$^7$, —CH=NNHC(NH)NH$_2$ or

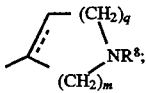

$R^4$ and $R^5$ are independently hydrogen or $C_{1-4}$alkyl;
$R^6$ and $R^7$ are the same or different and are each hydrogen or $C_{1-4}$alkyl or together with the nitrogen atom to which they are attached form a ring;
$R^8$ is hydrogen, $C_{1-4}$alkyl, or $C_{3-6}$alkenyl;
the dotted lines represent an optional bond; and
q and m are independently 1 or 2;
and pharmaceutically acceptable salts, solvates and hydrates thereof.

Suitably $A^1$ is O, S, NR or CH$_2$.

Suitably $A^2$ is a bond or CH$_2$.

Suitably $R^1$ is an optionally substituted 6- or 10-membered aryl ring such as phenyl or naphthyl.

Suitably $R^1$ is an optionally substituted 6- to 10-membered heteroaryl ring containing from 1 to 4 nitrogen atoms. Examples of such heteroaryl rings include pyridine, pyridazine, pyrimidine, pyrazine, triazine, quinoline, or quinazoline. Particular examples are pyridine, pyridazine, pyrimidine, pyrazine and quinoline.

The heteroaryl ring can be linked to $A^1A^2$ via a carbon or nitrogen atom of the heteroaryl ring.

Suitably $R^1$ is unsubstituted or substituted by up to 3 groups selected from halo, $C_{1-4}$alkyl, hydroxy, oxo, $C_{1-4}$alkoxy, —CO$_2$R$^9$, —NHCOR$^9$, —CONR$^{10}$R$^{11}$, —SO$_2$NR$^{10}$R$^{11}$, —NHSO$_2$R$^{12}$, NO$_2$, —NR$^{10}$R$^{11}$, —NHCONH$_2$, CN, CF$_3$ or CF$_3$O wherein $R^9$ to $R^{11}$ are independently hydrogen or $C_{1-4}$alkyl and $R^{12}$ is $C_{1-4}$alkyl.

Suitably, $R^2$ is hydrogen, halogen, $C_{1-4}$alkyl, CN, NO$_2$ or CF$_3$. Preferably $R^2$ is hydrogen or halogen, in particular hydrogen or chlorine.

Suitably $R^3$ is C(R$^4$)(R$^5$)CH$_2$NR$^6$R$^7$, or —CH=NNHC(NH)NH$_2$.

Suitably, $R^4$ and $R^5$ are hydrogen or $C_{1-4}$alkyl. Preferably $R^4$ and $R^5$ are both hydrogen or methyl.

Suitably, $R^6$ and $R^7$ are the same or different and are each hydrogen or $C_{1-4}$alkyl or together with the nitrogen atom to which they are attached form a ring. Preferably $R^6$ and $R^7$ are both hydrogen or methyl.

Suitable rings formed by $R^6$ and $R^7$ together with the nitrogen atom to which they are attached include for, example, 5- or 6-membered rings such as pyrrolidino and piperidino rings.

Suitably $R^3$ is a group

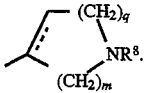

Examples of $C_{1-4}$alkyl groups (alone or as part of another group, e.g. $C_{1-4}$alkoxy) include methyl, ethyl, propyl or butyl which can be straight chain or branched.

Examples of halo groups include fluoro, bromo, chloro or iodo.

Particular compounds of structure (I) include:
3-(2-N,N-dimethylaminoethyl)-5-phenoxyindole,
3-(2-N,N-dimethylaminoethyl)-5-phenylthioindole,
1-amino-2-(5-(4-methoxyphenoxy)indol-3-yl)ethane,
1-(N,N-dimethylamino)-2-(5-(4-methoxyphenoxy)indol-3-yl)ethane,
1-amino-2-(5-(4-methylphenoxy)indol-3-yl)ethane,
1-(N,N-dimethylamino)-2-(5-(4-methylphenoxy)indol-3-yl) ethane,
1-amino-2-(5 -(3-trifluoromethylphenoxy)indol-3 -yl) ethane,
1-(N,N-dimethylamino)-2-(5-(3-trifluoromethylphenoxy) indol-3-yl)ethane,
1-(N,N-dimethylamino)-2-(4-chloro-5-phenoxyindol-3-yl) ethane,
3-(1-methyl-1,2,5,6-tetrahydropyrid-4-yl)-5-(4-methoxyphenoxy)indole,
3-(1-methyl-1,2,5,6-tetrahydropyrid-4-yl)-5-phenoxyindole,
3-(1-methyl-1,2,5,6-tetrahydropyrid-4-yl)-5-phenylthioindole,
1-amino-2-(5-(pyrid-3-yloxy)indol-3-yl)ethane,
1-(N,N-dimethylamino)-2-(5-(pyrid-3-yloxy)indol-3-yl) ethane, 1-amino-2-(5-(pyrimidin-2-yloxy)indol-3-yl) ethane, 1-(N,N-dimethylamino)-2-(5-(pyrimidin-2-yloxy)indol-3-yl)ethane, 3-(1-methyl-1,2,5,6-tetrahydropyrid-4-yl)-5-(pyrid-2-yloxy)indole, 1-(N,N-dimethylamino)-2-(5-(4-bromophenoxy)indol-3-yl)ethane, 1-(N,N-dimethylamino)-2-(5-(4-methoxypyrimidin-2-yloxy)indol-3-yl)ethane, 3-(1-methyl-1,2,5,6-tetrahydropyrid-4-yl)-5-(pyrid-2-ylthio)indole, 1-(N,N-dimethylamino)-2-(5-benzylindol-3-yl)ethane, and 4-chloro-3-(2-N,N-dimethylaminoethyl)-5-phenylthioindole, and, pharmaceutically acceptable salts, solvates or hydrates thereof.

Pharmaceutically acceptable acid addition salts of the compounds of structure (I) include, for example, those formed with inorganic acids e.g. hydrochloric, sulphuric, methanesulphonic or phosphoric acids and organic acids e.g. succinic, maleic, citric, (D) and (L) tartaric, acetic or fumaric acid. Other non-pharmaceutically acceptable salts e.g. oxalates may be used for example in the isolation of compounds of formula (I), and are included within the scope of this invention. Also included within the scope of the invention are solvates and hydrates of compounds of formula (I).

It will be appreciated that certain compounds of structure (I) for example where $R^4$ is other than hydrogen may contain an asymmetric centre. Such compounds will exist as two (or more) optical isomers (enantiomers). Both the pure enantiomers, racemic mixtures (50% of each enantiomer) and unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of structure (I) or a salt, solvate or hydrate thereof, which comprises:

(a) for compounds in which $R^3$ is $C(R^4)(R^5)CH_2NR^6R^7$ reduction of a compound of structure (II):

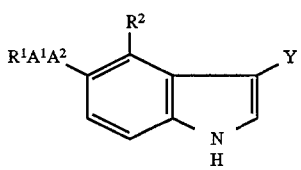

Structure (II)

(in which $A^1$, $A^2$, $R^1$ and $R^2$ are as described for structure (I) and Y is a reducible group) optionally in the presence of a compound of the formula $R^6R^7NH$ in which $R^6$ and $R^7$ are as described for structure (I); or (b) reaction of a compound of structure (III):

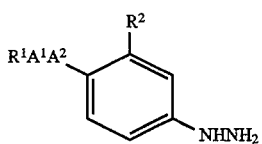

Structure (III)

(wherein $A^1$, $A^2$, $R^1$ and $R^2$ are as hereinbefore defined) or a salt thereof, with a compound of structure (IV):

 $R^3CH_2CHO$       Structure (IV)

or a protected derivative (e.g. an acetal or ketal) thereof wherein $R^3$ is as described for structure (I); or (c) for compounds where $R^3$ is

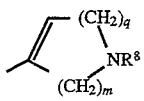

reaction of a compound of structure (V):

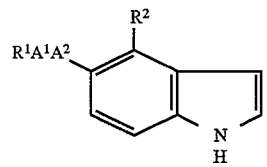

Structure (V)

(wherein $A^1$, $A^2$, $R^1$ and $R^2$ are as hereinbefore defined) with a compound of structure (VI):

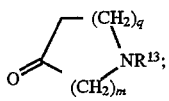

Structure (VI)

(wherein $R^{13}$ is a N-protecting group or $R^8$ as hereinbefore defined and q and m are as hereinbefore defined), and if required removing the N-protecting group; or (d) for compounds where $R^3$ is —CH=NNHC(NH)NH$_2$, reaction of a compound of structure (VII):

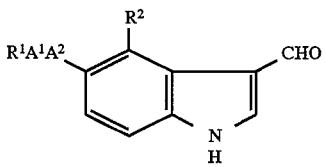

Structure (VII)

where $A^1$, $A^2$, $R^1$ and $R^2$ are as hereinbefore defined with aminoguanidine or an acid addition salt thereof;
and thereafter optionally converting a group $R^1$ into another group $R^1$;

converting a group $R^2$ into another group $R^2$;

forming a pharmaceutically acceptable salt or hydrate thereof.

In compounds of structure (II) Y may be a group which is converted to —C(R$^4$)(R$^5$)CH$_2$NR$^6$R$^7$ when reduced in the presence of R$^6$R$^7$NH, in which case examples of Y include —C(R$^4$)(R$^5$)CN; and —C(R$^4$)(R$^5$)CHO. Alternatively Y may be a group which itself can be reduced to —C(R$^4$)(R$^5$)CH$_2$NR$^6$R$^7$, such groups including —C(R$^4$)(R$^5$)CH$_2$NO$_2$, —C(R$^4$)(R$^5$)CH$_2$N$_3$, —COCONR$^6$R$^7$, —C(R$^4$)(R$^5$)CONR$^6$R$^7$, —C(R$^4$)=CHNO$_2$ and —C(R$^4$)(R$^5$)CH$_2$NR$^6$COR$^7$.

It will be appreciated that the precise method of reduction will depend on the nature of the group Y, such methods being well known in the art.

When Y represents —C(R$^4$)(R$^5$)CHO or —C(R$^4$)(R$^5$)CN the reaction between a compound of structure (II) and an amine R$^6$R$^7$NH is suitably carried out under reductive amination conditions, for example, catalytic hydrogenation in the presence of the amine R$^6$R$^7$NH and a suitable solvent. Suitable catalysts include, for example, Raney nickel. Suitable solvents include, for example, C$_{1-4}$alkanols, in particular methanol. The reaction is carried out at ambient temperature or elevated temperature for as long as is necessary for the reaction to be complete. Preferred reaction conditions include, for example for compounds in which R$^6$ and R$^7$ are both hydrogen, hydrogenation in methanolic ammonia in the presence of a Raney nickel catalyst; and where R$^6$ and R$^7$ are both $C_{1-4}$alkyl, for example methyl, hydrogenation in the presence of dimethylamine in methanol as solvent and Raney nickel as catalyst.

When Y represents a group —$C(R^4)(R^5)CH_2NO_2$, —$C(R^4)(R^5)CH_2N_3$, —$COCONR^6R^7$, or —$C(R^4)(R^5)$ $CONR^6R^7$ the reduction may be effected for example using allane (prepared from lithium aluminium hydride and sulphuric acid) or lithium aluminium hydride in a solvent such as tetrahydrofuran. Alternatively a group —$C(R^4)(R^5)$ $CH_2NO_2$ may be reduced by catalytic hydrogenation, using for example palladium on charcoal or by treatment with cobalt boride prepared by treating a cobalt II salt such as cobalt chloride with sodium borohydride in a suitable solvent such as methanol.

Reduction of a group —$C(R^4)(R^5)CH_2NR^6COR^7$ may be accomplished using a hydride such as lithium aluminium hydride.

It will be appreciated that a variety of other substituents Y and methods of reduction are well-known in tryptamine chemistry, such as those described in GB 2185020A, and may also be employed in process (a).

The intermediate compounds of structure (II) can be prepared by standard procedures.

Thus, compounds of structure (II) wherein Y represents —$CH_2CN$ may be prepared from the corresponding gramine (i.e. 3-dimethylaminomethyl) compound by cyanation e.g. using potassium cyanide. The gramine derivative may be obtained by reaction of the 3-unsubstituted indole with bisdimethylaminomethane in the presence of acetyl chloride and in a suitable solvent, such as dichloromethane. A 3-unsubstituted indole may be prepared from an appropriately substituted nitrotoluene derivative according to the following reaction scheme 1:

Scheme 1

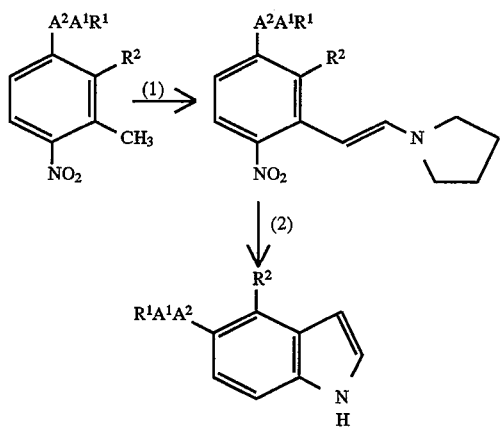

Structure (V)
(1) Me$_2$NCH(OEt)$_2$, DMF, pyrrolidine
(2) N$_2$H$_4$.H$_2$O, Ni.

Alternatively a 3-unsubstituted indole may be obtained from an appropriately substituted benzaldehyde derivative according to the following reaction scheme 2:

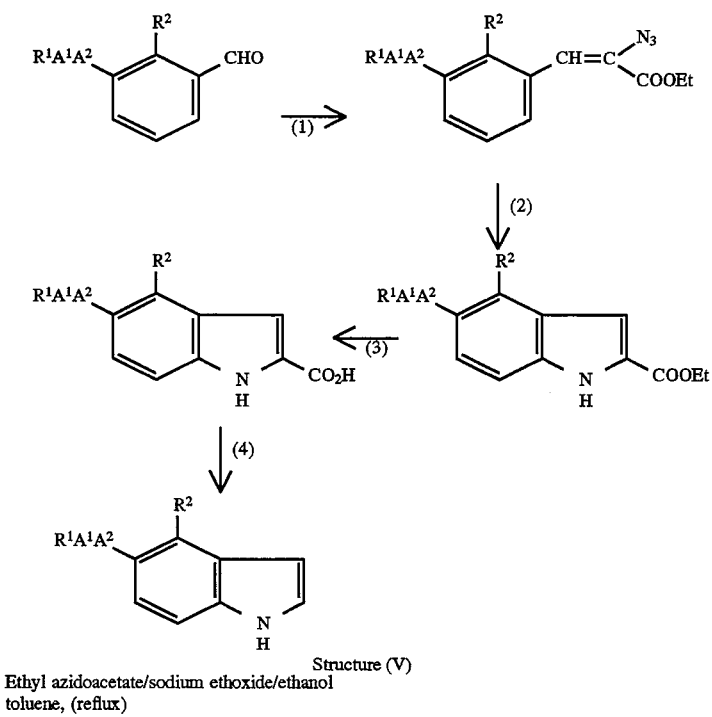

Structure (V)
(1) Ethyl azidoacetate/sodium ethoxide/ethanol
(2) toluene, (reflux)
(3) (i) Ethanol/sodium hydroxide (ii) HCl
(4) heating.

When Y represents —$C(R^4)(R^5)CH_2NR^6COR^7$ a compound of structure (II) may be prepared by reacting a corresponding aminoethyl compound with an acylating agent, for example an anhydride such as acetic or propionic anhydride or a mixture of an acid with an anhydride e.g. formic acid and acetic anhydride. This intermediate provides a convenient method of preparing compounds of structure (I) wherein one of $R^6$ and $R^7$ is hydrogen and the other a $C_{1-4}$alkyl group.

A compound of structure (II) wherein Y represents —$COCONR^6R^7$ may be prepared from an indole of structure (VIII):

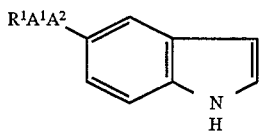

Structure (VIII)

by reaction with oxalyl chloride followed by an amine $HNR^6R^7$ and subsequently introducing the group $R^2$. When $R^2$ is halogen e.g. iodine this may be introduced by reaction of a compound of structure II where $R^2$ is H and Y is $COCONR^6R^7$ with an appropriate halide e.g. potassium iodide in an acidic medium such as trifluoroacetic acid in the presence of thallium trifluoroacetate.

A compound of structure (II) wherein Y represents —$C(R^4)(R^5)CHO$ may be prepared for example by oxidation of the corresponding alcohol, using an oxidising agent such as pyridinium chlorochromate, or dimethylsulphoxide with oxalylchloride and triethylamine.

The alcohol may itself be obtained by a cyclisation analogous to process (b). The alcohol may aim be converted to a halide derivative and thence to an azide using standard procedures, to give a compound of structure (II) wherein Y represents —$C(R^4)(R^5)CH_2N_3$.

A compound of structure (V) wherein $A^1A^2$ is S, $CH_2$, CH(OH), CH=CH, $CH(OH)CH_2$ or $CH_2CH_2$ can be prepared by reacting a compound of structure (IX):

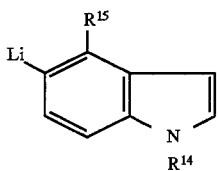

Structure (IX)

wherein $R^{14}$ is a N-protecting group and $R^{15}$ is a group $R^2$ as hereinbefore defined or a precursor thereof with an appropriate electrophile and thereafter removing the N-protecting group and thereafter if necessary converting a group $R^{15}$ to a group $R^2$.

Appropriate electrophiles include $R^1SSR^1$, $R^1(CH_2)_pL^1$ (wherein p is 1 or 2 and $L^1$ is a suitable leaving group such as halo, e.g. bromo or iodo), $R^1CHO$ or

The reaction with the epoxide results in compounds wherein $A^1A^2$ is $CH(OH)CH_2$ which can be dehydrated in the presence of acid to CH=CH. The reaction with the aldehyde results in compounds wherein $A^1A^2$ is CH(OH) which can be reduced for example by catalytic hydrogenation to $CH_2$.

Suitable N-protecting groups include trialkylsilyl groups in particular triisopropylsilyl which can be removed in standard manner, e.g. by treatment with tetra-n-butylammonium fluoride in a suitable solvent such as tetrahydrofuran or dichloromethane.

An example of a precursor of the group $R^2$ is hydrogen which is a suitable precursor for halogen as hereinbefore described for the introduction of such a group into a compound of structure (VIII).

A compound of structure (IX) can be suitably prepared by reacting a compound of structure (X):

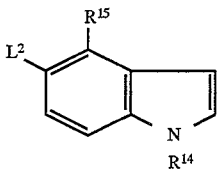

Structure (X)

wherein $L^2$ is a suitable leaving group such as halo, e.g. bromo or iodo and $R^{14}$ and $R^{15}$ are as hereinbefore defined with a lithiating reagent such as tert-butyl lithium or n-butyl lithium in a solvent such as diethyl ether or tetrahydrofuran at low temperature preferably –60° C.

The N-protecting group can be induced in standard manner, e.g. by treating with triisopropylsilyl chloride in dimethylformamide in the presence of sodium hydride as base.

A compound of structure (V) wherein $A^1A^2$ is S can be prepared by reacting a compound of structure (XI):

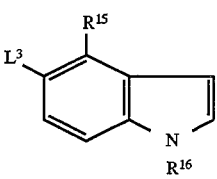

Structure (XI)

wherein $L^3$ is a suitable leaving group such as halo, e.g. bromo or iodo, or trifluoromethane sulphonyloxy, $R^{15}$ is as hereinbefore defined and $R^{16}$ is hydrogen or a group $R^{14}$ as hereinbefore defined with a compound of the formula $R^1SSn$ $(R^{17})_3$ where $R^{17}$ is $C_{1-4}$alkyl in the presence of a palladium catalyst such as palladium tetrakistriphenyl phosphine palladium (O) in an organic solvent such as toluene according to the method of M. Kosugi et al. Bull Chem Soc Jpn 1985, 58, 3657, and thereafter if required removing the group $R^{14}$ and/or converting a group $R^{15}$ to a group $R^2$.

A compound of structure (V) wherein $A^1A^2$ is $CH_2$, CH=CH or $CH_2CH_2$ can be prepared by reacting a compound of structure (XI) as hereinbefore defined with a compound of formula $R^1A^1A^2ZnX$ wherein X is halo such as chloro or bromo in the presence of a palladium catalyst such as palladium tetrakistriphenyl phosphine palladium (O) in an organic solvent such as tetrahydrofuran at ambient or preferably reflux temperature, and thereafter if required removing the group $R^{14}$ and/or converting a group $R^{15}$ to a group $R^2$.

A compound of structure (V) wherein $A^1A^2$ is CH=CH or $CH_2CH_2$ can be prepared by reacting a compound of structure (XI) as hereinbefore defined with a compound of formula $R^1CH=CH_2$ and thereafter if required reducing the product with for example palladium on charcoal under an atmosphere of hydrogen and/or removing the group $R^{14}$ and/or converting a group $R^{15}$ to a group $R^2$.

A compound of structure (V) wherein $A^1A^2$ is $OCH_2$, $SCH_2$ or $NRCH_2$ can be prepared by reacting a compound of structure (XII):

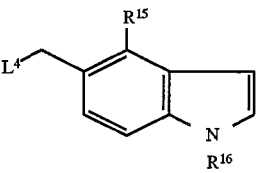

Structure (XII)

wherein $L^4$ is a suitable leaving group such as halo e.g. bromo or iodo, or trifluoromethane sulphonyloxy and $R^{15}$ and $R^{16}$ are as hereinbefore defined with a compound of formula R¹OH, R¹SH or R¹NHR in the presence of a suitable base such as potassium carbonate or potassium hydrogen carbonate in an organic solvent such as dimethylsulphoxide or dimethyl formamide at ambient or preferably reflux temperature, and thereafter if required removing the group R¹⁴ and/or converting a group R¹⁵ to a group R².

A compound of structure (V) wherein A¹A² is CH₂, SCH₂, CH(OH)CH₂, CH=CH or CH₂CH₂ can be prepared by reacting a compound of structure (XIII):

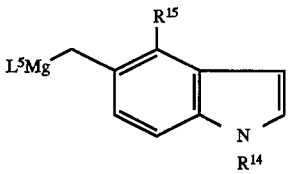

Structure (XIII)

wherein L⁵ is halo such as bromo or iodo and R¹⁴ and R¹⁵ are as hereinbefore defined with an appropriate electrophile and thereafter removing the N-protecting group and if required converting a group R¹⁵ to a group R². Appropriate electrophiles include R¹L¹, R¹SSR¹, R¹CHO or R¹CH₂L¹ wherein L¹ is as herebefore defined.

A compound of structure (XIII) can be prepared in standard manner by reacting a compound of structure (XII) wherein L⁴ is halo and R¹⁶ is a group R¹⁴ with magnesium.

A compound of structure (V) wherein A¹A² is O, S or NR can be prepared by reacting optionally in the presence of a suitable base such as potassium hydroxide a compound of structure (XIV):

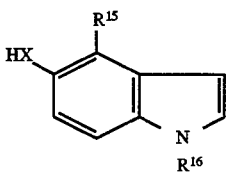

Structure (XIV)

wherein X is O, S or NR and R¹⁵ and R¹⁶ are as hereinbefore defined with a compound of formula R¹L¹ wherein R¹ is as hereinbefore defined and its nature allows nucleophillic aromatic substitution and L¹ is a suitable leaving group such as halo, and thereafter if required removing the group R¹⁴ and/or converting a group R¹⁵ to the group R².

The chemistry hereinbefore described for preparing a compound of structure (V) can be similarly used for preparing a compound of structure (XV):

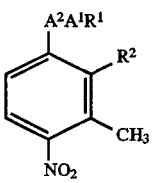

Structure (XV)

which is the starting material of Scheme 1, except that instead of the compounds of structure (XI) or (XII) are used compounds of structure (XVI):

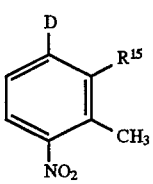

Structure (XVI)

wherein D is L³ or L⁴CH₂ and L³, L⁴ and R¹⁵ are as hereinbefore defined.

A compound of structure (XV) wherein A¹A² is O, S or NR can be prepared by reacting a compound of structure (XVI) wherein D is fluoro with R¹OH, R¹SH or R¹NHR in a dipolar aprotic solvent such as dimethyl sulphoxide or dimethylformamide in the presence of a base such as potassium carbonate at ambient or preferably elevated temperatures in particular the boiling point of the solvent, and thereafter if required converting a group R¹⁵ to a group R².

Cyclisation according to process (b) is a standard method for preparing indole compounds and may be effected by methods well known in the art, for example by heating a compound of structure (III) with a compound of structure (IV) in a non-aqueous solvent such as acetic acid or an aqueous or non-aqueous solvent e.g. an alcohol such as methanol in the presence of an acid catalyst such as hydrochloric acid or a Lewis acid such as boron trifluoride, or in the presence of an acidic ion exchange resin.

A compound of structure (III) may be obtained from the corresponding aniline derivative by diazotisation, for example using sodium nitrite and concentrated hydrochloric acid, and subsequent reduction.

In process (c) the reaction of a compound of structure (V) with a compound of structure (VI) is suitably performed in the presence of a base e.g. sodium methoxide in an organic solvent such as a C₁₋₂alkanol at ambient temperature or elevated temperature e.g. 30°–50° C., conveniently at the reflux temperature of the reaction mixture. Alternatively the reaction can be carried out under acidic conditions, e.g. in acetic acid at elevated temperature (e.g. 30°–100° C.). When R¹³ is a N-protecting group for example tert-butoxycarbonyl this can be removed in standard manner for example by treatment with HCl in methanol or with trifluoroacetic acid.

In process (d) a compound of the structure (VII) is suitably reacted with an acid addition salt of aminoguanidine, e.g. the hydrochloride, in a suitable solvent such as a C₁₋₄alkanol, e.g. methanol or ethanol at ambient or preferably elevated temperature, e.g. 30°–100° C., conveniently at the reflux temperature of the reaction mixture.

A compound of the structure (VII) can suitably be prepared by reacting a compound of structure (V) as hereinbefore defined with a Vilsmeier reagent formed from phosphoryl chloride and dimethylformamide followed by aqueous work-up in the presence of a base such as sodium hydroxide.

Suitable interconversions of R¹ groups, and of R² groups, will be apparent to those skilled in the art and can be carried out by standard procedures.

Acid addition salts of compounds (I) can be prepared by standard procedures, for example, by reaction with suitable organic and inorganic acids, the nature of which will be apparent to persons skilled in the art.

Compounds of structure (I) have affinity for the 5-HT₁ -like receptor and are expected to be useful in treating disease states which require modulation of the 5-HT₁ -like receptor. In particular the compounds are 5-HT₁ -like agonists (or partial agonists) and as such are expected to have utility in medicine in the treatment and/or prophylaxis of migraine, and other conditions associated with cephalic pain, such as cluster headache, headache associated with vascular disorders and other neuralgia. They are also expected to have utility in the treatment or prophylaxis of portal hypertension.

In a further aspect, the invention provides a method of treatment of conditions which require alteration of the 5-HT₁-like receptor in particular migraine or portal hypertension which comprises administering to a subject in need thereof an effective amount of a compound of structure (I) or a pharmaceutically acceptable salt, solvate or hydrate thereof.

For use in medicine, the compounds of the present invention are usually administered in a standard pharmaceutical composition. The present invention therefore provides in a further aspect pharmaceutical compositions comprising a compound of structure (I) or a pharmaceutically acceptable salt, solvate or hydrate thereof and a pharmaceutically acceptable carrier.

The compounds of the invention may be administered by any convenient route, for example by oral, parenteral, buccal, sublingual, nasal, rectal or transdermal administration and the pharmaceutical compositions adapted accordingly.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, preferably between 10 mg and 400 mg e.g. between 10 mg and 250 mg, or an intravenous, subcutaneous, or intramuscular dose of between 0.1 mg and 100 mg, preferably between 0.1 mg and 50 mg e.g. between 1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

BIOLOGICAL DATA

5-HT$_1$-like Receptor Screen

RABBIT BASILAR ARTERY

Experiments were performed in intracranial arteries from rabbit isolated basilar artery in a similar method to one described previously (Parsons and Whalley, 1989. Eur J Pharmacol 174, 189–196.).

In brief, rabbits were killed by overdose with anaesthetic (sodium pentobarbitone). The whole brain was quickly removed and immersed in ice cold modified Kreb's solution and the basilar artery removed with the aid of a dissecting microscope. The Krebs solution was of the following composition (mM) Na$^+$ (120); K$^+$ (5); Ca$^{2+}$ (2.25); Mg$^{2+}$ (0.5); Cl$^-$ (98.5); SO$_4^{2-}$ (1); EDTA (0.04), equilibrated with 95% O$_2$/5% CO$_2$. The endothelium was removed by a gentle rubbing of the lumen with a fine metal wire. Arteries were then cut into ring segments (ca 4–5 mm wide) and set up for recording of isometric tension in 50 ml tissue baths in modified Krebs solution with the additional supplement of (mM); Na$^{2+}$ (20); fumarate (10); pyruvate (5); L-glutamate (5) and glucose (10). The arteries were then placed under a resting force of 3–4 mN maintained at 37° C. and the solution bubbled with 95% O$_2$/5% CO$_2$.

After tests for initial reactivity with 90 mM KCl depolarising solution and for lack of acetylcholine-induced relaxation of 5-HT (10 mM) precontraction, cumulative concentration-effect curves (2 nM-60 mM) to 5-HT were constructed in the presence of ascorbate 200 mM, cocaine 6 mM, indomethacin 2.8 mM, ketanserin 1 mM and prazosin 1 mM.

Following a 45–60 min wash period, cumulative concentration-effect curves to the test compounds or 5-HT (as a time match control) were constructed in the presence of ascorbate, indomethacin, cocaine, ketanserin and prazosin.

The compounds of Examples 1, 2, 3A, 3B, 4A, 8, 10B, 12 and 16 had EC$_{50}$ values (concentration for half-maximal contraction) in the range 0.025 to 4.2 µM.

EXAMPLE 1

3-(2-N,N-Dimethylaminoethyl)-5-phenoxyindole (a) A mixture of 5-fluoro-2-nitrotoluene (9.8 g), phenol (11.89 g), potassium carbonate (12.22 g) and copper bronze (1.0 g) was boiled for 16 hours. After cooling to room temperature the mixture was extracted with boiling diethyl ether (2×500 ml) and the combined organic phases washed with aqueous 1N sodium hydroxide (6×100 ml) and water (3×100 ml). After drying (MgSO$_4$), solvent was removed at reduced pressure and the residue column chromatographed (silica gel, hexane→5% diethyl ether/hexane eluant) to give 2-nitro-5-phenoxytoluene (2.06 g) as an oil.

$^1$H NMR (CDCl$_3$) 2.59(s,3H), 6.81–6.85(m,2H), 7.06(d, 2H), 7.23–7.27(m,1H) 7.38–7.46(m,2H) and 8.04(m,1H).

(b) A solution of 2-nitro-5-phenoxytoluene (2.06 g) in dimethylformamide (30 ml) containing dimethylformamide diethylacetal (1.57 g) and pyrrolidine (0.77 g) was heated at 120° C. for 2 hours. Solvent was removed at reduced pressure and the residue dissolved in methanol. Raney Nickel (one spatula measure) was added followed by hydrazine hydrate (3×0.5 ml portions, one portion every 30 minutes). The mixture was stirred for a further 1 hour after the final portion of hydrazine hydrate was added, the mixture filtered and solvent removed at reduced pressure. The residue was partitioned between water (100 ml) and diethyl ether (100 ml), the organic phase separated and dried (MgSO$_4$), solvent removed at reduced pressure and the residue column chromatographed (silica gel, hexane →10% ethyl acetate/hexane eluant) to give 5-phenoxyindole (0.52 g).

$^1$H NMR (d$_6$-DMSO) 6.40(m,1H), 6.80–6.91(m,3H), 7.02 (t,1H), 7.20(m, 1H), 7.26–7.44(m,4H) and 11.16(br.s,1H).

(c) To a cooled (ice bath) solution of bis (dimethylamino) methane (0.34 g) in dichloromethane (25 ml), acetyl chloride was added dropwise over 5 minutes. After stirring for 10 minutes, 5-phenoxyindole (0.51 g) was added and stirring continued for a further one hour at room temperature. The mixture was basified with aqueous 2N sodium hydroxide, brine (50 ml) added and the organic phase separated washed with water (2×50 ml), dried (MgSO$_4$) and the solvent removed at reduced pressure. The residue was dissolved in dimethylformamide (25 ml) and potassium cyanide (0.62 g) and iodomethane (0.61 g) added. After stirring for 48 hours, the mixture was diluted with water (50 ml) and extracted with ethyl acetate (3×50 ml). The combined organic phases were washed with water (4×50 ml), dried (MgSO$_4$) and solvent removed at reduced pressure to give 3-cyanomethyl-5-phenoxyindole (0.57 g).

$^1$ H NMR (d$_6$-DMSO) 4.01(s,2H), 6.87–6.92(m,3H), 7.03 (t,1H), 7.28–7.45(m,5H)

(d) To a solution of 3-cyanomethyl-5-phenoxyindole (0.57 g) in methanol (25ml) containing dimethylamine (10 ml) Raney nickel (one spatula) was added and the mixture shaken under 45 psi hydrogen pressure for 2 hours. The catalyst was removed by filtration, solvent removed at reduced pressure and the residue column chromatographed (silica gel, dichloromethane/10% methanol in ammonia 0→8% eluant) to give the title compound (0.035 g) from which the oxalate salt was prepared by the addition of oxalic acid (0.024 g) in methanol (1 ml) followed by diethyl ether to the cloud point to give the oxalate salt m.p. 170°–173° C.

EXAMPLE 2

3-(2-N,N-Dimethylaminoethyl)-5-phenylthioindole (a) Triisopropylsilyl chloride (6.87 g) was added to the sodium salt prepared from 5bromoindole (6.35 g) and sodium hydride (1.71 g, 50% suspension in oil) in dimethylformamide (32 ml) and the mixture was stirred at room temperature for 2 hours then poured into ice water (150 ml). The crude intermediate obtained by evaporation of the dichloromethane extract was column chromatographed (silica gel, 40°–60° C. petroleum ether) to give 5-bromo-1-triisopropylsilylindole isolated as an oil.

(b) 5-Bromo-1-triisopropylsilylindole (6.74 g) was dissolved in tetrahydrofuran (100 ml) cooled (CO$_2$/acetone) and tert butyl lithium (40 ml, 1.7M in pentane) added over 30 minutes. Stirring of the deep yellow solution was continued for a further 1 hour, diphenyl disulphide (21 g) in tetrahydrofuran (30 ml) added, the mixture warmed to room temperature overnight, tetrabutylammonium fluoride (50 ml, 1M in tetrahydrofuran) added and stirring continued for a further 2 hours. Water (200 ml) was added and the mixture extracted with diethyl ether (3×100 ml). The combined organic phase was washed with brine (100 ml) dried (MgSO$_4$) and the solvent removed at reduced pressure. The residue was column chromatographed (silica gel, hexane/ diethyl ether 0–40% eluant) appropriate fractions combined, solvent removed and the residue recrystallised from hexane/ diethyl ether to give 5-phenylthioindole (2.21 g) m.p.97°–99° C.

(c) Oxalyl chloride (0.57 g) in diethyl ether ((2 ml) was added dropwise over 5 minutes to 5-phenylthioindole (0.75 g) in diethyl ether (10 ml) with ice cooling. After stirring for 1 hour the precipitated solid was collected by filtration dissolved in dichloromethane (40 ml) and a saturated solution of dimethylamine in diethyl ether (4 ml) added. After stirring for 1 hour the mixture was diluted with dichloromethane (40 ml) and washed with 10% aqueous potassium carbonate (2×ml) water (2×30 ml) and brine (30 ml). The organic phase was dried (MgSO$_4$) and the solvent removed at reduced pressure. The residue was triturated with ethyl acetate/diethyl ether to give 3-N,N-dimethylglyoxamido-5-phenylthioindole (0.78 g), m.p. 163°–166° C.

(d) To a solution of 3-N,N-dimethylglyoxamido-5-phenylthioindole (0.4 g) in tetrahydrofuran (70 ml) alane [prepared from lithium aluminium hydride (0.76 g) and conc. sulphuric acid (1.0 g) in tetrahydrofuran (50 ml)] was added and the mixture stirred for 16 hours. After quenching by the dropwise addition of water the mixture was filtered (celite pad) and solvent removed at reduced pressure. The residue was partitioned between dichloromethane (50 ml) and 1M hydrochloric acid (50 ml). The organic phase was separated, dried (MgSO$_4$) and the solvent removed at reduced pressure. The residue was triturated with diethyl ether/ethyl acetate to give the title compound (0.20 g) m.p. softens >162° C.

$^1$H NMRδ(d$_6$-DMSO) 2.81(s,6H), 3.12(m,2H), 3.30(m, 2H), 7.06(d,2H), 7.12(t,1H), 7.23(m,3H), 7.35(s,1H), 7.46 (s,1H), 7.91(s,1H), 10.36(br.s, 1H) and 11.32(s,1 H).

EXAMPLE 3

1-Amino-2-(5-(4-methoxyphenoxy)indol-3-yl)ethane (3A) and 1-(N,N-dimethylamino)-2-(5-(4-methoxyphenoxy)indol-3-yl)ethane (3B)

a) Sodium metal (2.01 g, 87.43 mmol) cut into small pieces was dissolved in absolute ethanol (67 mL) and the resulting solution cooled to −5° C. A mixture of ethyl azidoacetate (11.32 g, 87.67 mmol) and 3-(4-methoxyphenoxy) benzaldehyde (5.0 g, 21.91 mmol) was added dropwise over 30 min. On completion of addition the mixture was stirred at −5° C. for 4.5 hr, and then kept at room temperature overnight. The red reaction mixture was poured into saturated aqueous NH$_4$Cl solution and extracted (3×) with Et$_2$O. The ethereal extracts were washed (H$_2$O and then saturated aqueous NaCl), dried (MgSO$_4$) and evaporated to give an orange gum which was chromatographed (silica gel; hexane/Et$_2$O; 0–15%). The product: ethyl 2-azido-3-(3-(4-methoxyphenoxy)phenyl)propenoate, was thus obtained as a light yellow gum, 5.5 g (70%).

b) The vinyl azide (4.40 g, 12.97 mmol) was dissolved in dry, redistilled xylene (250 mL) and added dropwise to refluxing xylene (280 mL) under an atmosphere of nitrogen. Once addition was complete, reflux was maintained for 4.5 hr. After cooling, the xylene was evaporated in vacuo and the resulting yellow solid was chromatographed (silica gel; hexane/Et$_2$O; 0–21%). Two products were obtained: (i) ethyl 7-(4-methoxyphenoxy)indole-2-carboxylate, (R$_f$=0.35; hexane/Et$_2$O) colourless plates ex hexane, 0.957 g (24%), and (ii) ethyl 5-(4-methoxyphenoxy)indole-2-carboxylate, (R$_f$=0.19; hexane/Et$_2$O) colourless needles ex hexane/toluene (3:1 ), 1.661 g (41%).

c) Ethyl 5-(4-methoxyphenoxy)indole-2-carboxylate (1.60 g, 5.14 mmol) was heated in methanolic NaOH (3.2M, 9.1 mL), at reflux for 1 hr. The resulting thick paste was added to water and brought to pH 2 with 5M HCl. The flocculent precipitate of acid thus formed was extracted into EtOAc (3×) and the combined organic layers washed with saturated aqueous NaCl, dried (MgSO$_4$) and evaporated to give, as an off-white solid: 5-(4-methoxyphenoxy)indole-2-carboxylic acid, 1.40 g (96%).

d) The carboxylic acid (1.3 g, 4.59 mmol) was suspended in dry Et$_2$O, and the mixture cooled in a dry-ice/acetone bath. Pre-condensed liquid ammonia (ca 20 mL) was added, and the mixture was stirred. The cooling was removed and the mixture allowed to warm to room temperature, while the excess ammonia evaporated. The remaining ether was evaporated in vacuo leaving the ammonium salt as a coating around the inside of the flask. This was then fitted with an air condenser and, under an atmosphere of N$_2$, the flask was heated over a microburner. The solid melted and darkened, and vigourous gas evolution was observed. After cooling the material was dissolved in CH$_2$Cl$_2$ and washed with aq. K$_2$CO$_3$ solution (2×) followed by brine, dried (MgSO$_4$) and evaporated to a dark oil which was distilled (kugelrohr; 250° C. at ca 0.5 mbar) giving: 5-(4-methoxyphenoxy)indole as a colourless oil which solidified to a crystalline mass on standing, 0.95 g (87%).

e) N,N,N',N'-Tetramethyldiaminomethane (0.29 g, 0.39 mL, 2.82 mmol) was dissolved in CH$_2$Cl$_2$ (dry; 8.5 mL) and the stirred solution cooled in an ice-bath. Acetyl chloride (0.23 g, 0.21 mL, 2.95 mmol) was added dropwise (syringe) over 10 min, to give a white suspension. After stirring for a further 20 min. with cooling maintained, a solution of 5-(4-methoxyphenoxy)indole (0.5 g, 2.09 mmol) in CH$_2$Cl$_2$ (7.2 mL) was added dropwise, over 20 min. The cooling was removed and the resulting clear solution was stirred for 1 hr at room temperature. The solution was then diluted with CH$_2$Cl$_2$, washed with 10% aq. NaOH (2×) followed by saturated aqueous NACl and dried (MgSO$_4$). Evaporation in vacuo gave 3-(N,N-dimethylaminomethyl)-5-(4-methoxyphenoxy)indole as a gum. This material was dissolved in DMF (dry; 7 mL) and potassium cyanide (0.52 g, 8.0 mmol) was added, followed by methyl iodide (1.19 g, 0.52 mL, 8.35 mmol). The mixture became cloudy and eventually opaque. After stirring at room temperature for 36 hr, water was added and the mixture was extracted with Et$_2$O (2×). The combined organic layers were washed with H$_2$O (2×) and then with saturated aqueous NaCl, dried (MgSO$_4$) and evaporated to give an almost colourless gum. This was triturated with Et$_2$O to give: 3-cyanomethyl-5-(4-methoxyphenoxy)indole as a virtually colourless solid, 0.334 g (57%).

f) The cyanomethyl compound (0.31 g, 1.114 mmol) was dissolved in MeOH (15 mL) and the solution cooled (dry-ice/acetone bath). Pre-condensed dimethylamine (ca 15 mL) was added, followed by Raney nickel (one spatula). The mixture was hydrogenated at ca 45 psi (room temperature) for 1.5 hr. The catalyst was filtered off, and the filtrate evaporated to a gum, This was dissolved in $^i$PrOH (10 mL) and treated with di-tert-butyl dicarbonate (0.25 g, 1.15 mmol). After stirring at room temperature for 1 hr, the mixture was evaporated to a gum, which was chromatographed (silica gel; hexane/Et$_2$O; 0–60% and then CH$_2$Cl$_2$/EtOH containing 2% concentrated aqueous NH$_3$; 0–18%). Two products were obtained: (i) 1-tert-butoxycarbonylamino-2-(5-(4-methoxyphenoxy)indol-3-yl) ethane; a colourless gum, (0.088 g, 21%) which eluted in 60% Et$_2$O/hexane, and (ii) 1-(N,N-dimethylamino)-2-(5-(4-methoxyphenoxy)indol-3-yl)ethane; a gum (0.166 g, 48%), which required the more polar eluant described above. The less polar product was dissolved in MeOH (0.5 mL) and treated with ethereal HCl (1.0M, 2 mL). After standing at ca 4° C. for 2 hr, the solution was evaporated to dryness. The residue was redissolved in MeOH (0.5 mL) and on addition of Et$_2$O small, slightly pink plates were obtained of: 1-amino-2-(5-(4-methoxyphenoxy)indol-3-yl)ethane hydrochloride (3A), 0.054 g, (15%), m.p. 207°–26° C. (decomp.). The more polar column fraction was dissolved in methanol and treated with oxalic acid (0.10 g, 1.11 mmol). Addition of Et$_2$O to the pale yellow solution gave, as small, slightly off-white crystals: 1-(N,N-dimethylamino)-2-(5-(4-methoxyphenoxy)indol-3-yl)ethane oxalate (3B), 0.116 g (26%), m.p. 166°–70° C.

In a similar manner to that described above for Examples 3A and 3B, the following pairs of compounds were synthesised.

EXAMPLE 4

1-Amino-2-(5-(4-methylphenoxy)indol-3-yl)ethane (4A) and 1-(N,N-dimethylamino)-2-(5-(4-methylphenoxy)indol-3-yl)ethane (4B)

a) As previously described, sodium ethoxide was prepared from sodium metal (2.16 g, 93.95 mmol) in EtOH (72 mL) and after cooling, a mixture of ethyl azidoacetate (12.17 g, 94.25 mmol) and 3-(4-methylphenoxy)benzaldehyde (5.0 g, 23.56 mmol) was added. After 4.5 hr the reaction was worked-up, and chromatography (silica gel; hexane/Et$_2$O; 0–5%) gave the product: ethyl 2-azido-3-(3-(4-methylphenoxy)phenyl)propenoate as a yellow oil, 4.50 g (59%).

b) The azide (3.38 g, 10.46 mmol) in xylene (170 mL) was added to refluxing xylene (180 mL) under an atmosphere of N$_2$. After refluxing for 3.5 hr the solution was cooled and evaporated, and the residue was chromatographed (silica gel; hexane/Et$_2$O) to give two products: (i) ethyl 7-(4-methylphenoxy)indole-2-carboxylate, colourless needles from hexane, 0.797 g (20%), and (ii) ethyl 5-(4-methylphenoxy)indole-2-carboxylate, colourless crystals from hexane/toluene, 1.752 g (43%).

c) Ethyl 5-(4-methylphenoxy)indole-2-carboxylate (1.0 g, 3.39 mmol) was hydrolysed in methanolic NaOH (3.2M, 6.0 mL) at reflux, for 1 hr. After work-up the product: 5-(4-methylphenoxy)indole-2-carboxylic acid was obtained as an almost white solid, 0.92 g (ca 100%).

d) The carboxylic acid (0.72 g, 2.69 mmol) was converted to its ammonium salt, which was heated (microburner) to give a dark oil. This was distilled (kugelrohr, 250° C. at ca 1 mbar) giving 5-(4-methylphenoxy)indole, a colourless gum, which solidified on storage in the freezer, 0.417 g (70%).

e) Treatment of a cooled solution of N,N,N',N'-tetramethyldiaminomethane (0.24 g, 0.32 mL, 2.35 mmol) in $CH_2Cl_2$ (7 mL) with acetyl chloride (0.19 g, 0.17 mL, 2.39 mmol) followed by a solution of 5-(4-methylphenoxy)indole (0.39 g, 1.74 mmol) in $CH_2Cl_2$ (6 mL), gave after work-up: 3-(N,N-dimethylaminomethyl)-5-(4-methylphenoxy)indole as a gum. This was treated with potassium cyanide (0.43 g, 6.6 mmol) and methyl iodide (0.98 g, 0.43 mL, 6.9 mmol) in DMF (6 mL) for 16 hr, and after appropriate work-up, 3-cyanomethyl-5-(4-methylphenoxy)indole was obtained as an off-white crystalline solid 0.338 g (74%).

f) The cyanomethyl compound (0.324 g, 1.235 mmol) was hydrogenated in MeOH (9 mL) and $Me_2NH$ (7 mL) over Raney nickel, at room temperature and 45 psi. After work-up and treatment with $BOC_2O$ (excess) in $^iPrOH$, evaporation gave a gum which was chromatographed (silica gel; hexane/ $Et_2O$; 0–50% and then $CH_2Cl_2/EtOH$ containing 2% concentrated aqueous $NH_3$; 0–14%). Two products were obtained: (i) 1-tert-butoxycarbonylamino-2-(5-(4-methylphenoxy)indol-3-yl)ethane; a gum (0.12 g) and (ii) 1-(N,N-dimethylamino)-2-(5-(4-methylphenoxy) indol-3-yl)ethane; a gum (0.19 g). Treatment of the less polar compound with $HCl/Et_2O$ in MeOH gave, as a faintly mauve crystalline solid: 1-amino-2-(5-(4-methylphenoxy)indol-3-yl)ethane hydrochloride (4A), 0.063 g (17%), m.p. 230°–34° C. The more polar column fraction, on treatment with oxalic acid (0.11 g) in MeOH (ca 1.5 mL) followed by addition of $Et_2O$, gave: 1-(N,N-dimethylamino)-2-(5-(4-methylphenoxy)indol-3-yl)ethane oxalate (4B), off-white granular crystals, 0.12 g (25%), m.p. 148°–52° C.

EXAMPLE 5

1-Amino-2-(5-(3-trifluoromethylphenoxy)indol-3-yl) ethane (5A) and 1-(N,N-dimethylamino)-2-(5-(3-trifluoromethylphenoxy)indol-3-yl)ethane (5B)

a) As previously described, sodium ethoxide was prepared from sodium metal (1.58 g, 68.73 mmol) in EtOH (53 mL) and after cooling, a mixture of ethyl azidoacetate (8.93 g, 69.16 mmol) and 3-(3-trifluoromethylphenoxy) benzaldehyde (4.6 g, 17.28 mmol) was added. After 16 hr the reaction was worked-up, and chromatography (silica gel; hexane/$Et_2O$; 0–3%) gave the product: ethyl 2-azido-3-(3-(3-trifluoromethylphenoxy)phenyl)propenoate as a yellow oil, 3.52 g (54%).

b) The azide (3.50 g, 9.28 mmol) in xylene (150 mL) was added to refluxing xylene (172 mL) under an atmosphere of $N_2$. After refluxing for 2 hr the solution was cooled and evaporated; and the residue was chromatographed (silica gel; hexane/$Et_2O$) to give two products: (i) ethyl 7-(3-trifluoromethylphenoxy)indole-2-carboxylate, colourless prisms from hexane, 0.886 g (27%), and (ii) ethyl 5-(3-trifluoromethylphenoxy)indole-2-carboxylate, colourless needles from hexane/toluene, 1.062 g (33%).

c) Ethyl 5-(3-trifluoromethylphenoxy)indole-2-carboxylate (0.8 g, 2.29 mmol) was hydrolysed in methanolic NaOH (3.2M, 4.0 mL) at reflux, for 1 hr. After work-up the product: 5-(3-trifluoromethylphenoxy)indole-2-carboxylic acid was obtained as an almost white solid, 0.73 g (ca 100%).

d) The carboxylic acid (0.73 g, 2.27 mmol) was convened to its ammonium salt, which was heated (microburner) until tlc of the resulting dark oil showed consumption of starting material. This oil was distilled (kugelrohr, 225° C. at ca 0.8 mbar) giving: 5-(3-trifluoromethylphenoxy)indole, a virtually colourless oil, 0.537 g (85%).

e) Treatment of a cooled solution of N,N,N',N'-tetramethyldiaminomethane (0.26 g, 0.34 mL, 2.50 mmol) in $CH_2Cl_2$ (7.3 mL) with acetyl chloride (0.20 g, 0.18 mL, 2.53 mmol) followed by a solution of 5-(3-trifluoromethylphenoxy) indole (0.50 g, 1.79 mmol) in $CH_2Cl_2$ (6.2 mL), gave after work-up: 3-(N,N-dimethylaminomethyl)-5-(3-trifluoromethylphenoxy)indole as a gum. This was treated with finely ground potassium cyanide (0.45 g, 6.9 mmol) and methyl iodide (1.03 g, 0.45 mL, 7.26 mmol) in DMF (9 mL) for 16 hr, and after appropriate work-up and chromatography (silica gel; hexane/$Et_2O$; 0–45%) 3-cyanomethyl-5-(3-trifluoromethylphenoxy)indole was obtained as an almost colourless gum, 0.415 g (73%).

f) The cyanomethyl compound (0.4 g, 1.27 mmol) was hydrogenated in MeOH (18 mL) and $Me_2NH$ (14 mL) over Raney nickel, at room temperature and 40 psi. After work-up and treatment with $BOC_2O$ (excess) in $^iPrOH$, evaporation gave a gum which was chromatographed (silica gel; hexane/ $Et_2O$; 0–60% and then $CH_2Cl_2/EtOH$ containing 2%) $NH_3$; 0–22%). Two products were obtained: (i) 1-tert-butoxycaxbonylamino-2-(5-(3-trifluoromethylphenoxy (indol-3-yl)ethane; a colourless gum (0.069 g) and (ii) 1-(N,N-dimethylamino)-2-(5-(3-trifluoromethylphenoxy) indol-3-yl)ethane; a gum (0.21 g). Treatment of the less polar compound with $HCl/Et_2O$ in MeOH gave, as white crystalline powder 1-amino-2-(5-(3-trifluoromethylphenoxy)indol-3-yl)ethane hydrochloride (5A), 0.023 g,(5%), m.p. 200°–08° C. The more polar column fraction, on treatment with oxalic acid (0.083 g) in MeOH, followed by addition of $Et_2O$, gave small white crystals of: 1-(N,N-dimethylamino)-2-(5-(3-trifluoromethylphenoxy)indol-3-yl)ethane oxalate (5B), 0.151 g (27%), m.p. 169°–72° C.

EXAMPLE 6

1-(N,N-Dimethylamino)-2-(4-chloro-5-phenoxyindol-3-yl)ethane a) 3-Phenoxybenzoic acid (20.0 g, 93.36 mmol) was added portionwise to thionyl chloride (20 mL) and the resulting mixture was refluxed for 1.5 hr. After cooling, the excess $SOCl_2$ was evaporated in vacuo to give the crude acid chloride as a brown oil. This was dissolved in $CH_2Cl_2$/THF (1:3; 95 mL) and the solution added dropwise to a stirred, ice cooled solution of 2-amino-2-methyl propan-1-ol in $CH_2Cl_2$ (185 mL), maintained under an atmosphere of $N_2$. The reaction mixture was stirred at room temperature for ca 16 hr, and was then washed with water (2×) and saturated aqueous NaCl, dried ($MgSO_4$) and evaporated to a gum. This material was cooled (ice-bath) and thionyl chloride (18 mL) was added dropwise, with stirring. The reaction mixture became warm and vigourous gas evolution was observed. After stirring at room temperature for 0.5 hr, the excess $SOCl_2$ was evaporated in vacuo. The residue was suspended in water and while cooling in an ice-bath, 20% NaOH aq. was added to ca pH 13. The mixture was extracted (2×) with $CH_2Cl_2$ and the combined extracts were washed with water (2×) and saturated aqueous NaCl, dried ($MgSO_4$) and evaporated to a gum. This was chromatographed (silica gel; hexane/$Et_2O$) to give two products:

(i) 2-(3-phenoxyphenyl)-4,4-dimethyl-4,5-dihydrooxazole, ($R_f$=0.42, 3:1 hexane/$Et_2O$) a pale yellow oil, 12.72 g (51%) and (ii) 2-(3-phenoxybenzamido)-2-methylpropyl benzoate. ($R_f$=0.26, 3:1 hexane/$Et_2O$) a pale yellow viscous gum, 8.98 g (20%).

b) 2-(3-Phenoxyphenyl)-4,4-dimethyl-4,5-dihydrooxazole (4.5 g, 16.83 mmol) was dissolved in THF (43 mL) and the solution was cooled to –65° C. "BuLi (2.5M in hexane; 9.5 mL) was added (syringe) at an appropriate rate to maintain the temperature below –60° C. The resulting orange-yellow solution was stirred at –65° C. for 45 min. and then a solution of N-chlorosuccinimide (2.25 g, 16.85 mmol) in THF (35 mL) was added, again ensuring that the temperature did not rise above –60° C. The mixture was allowed to warm gradually to room temperature and stirred overnight. After quenching with water and evaporation of the bulk of the THF in vacuo, the biphasic mixture was extracted with $Et_2O$ (2×). The combined ethereal extracts were washed with $H_2O$ and then saturated aqueous NACl, dried ($MgSO_4$) and evaporated to a gum which was chromatographed (silica gel; hexane/$Et_2O$; 0–17%) to afford two compounds: firstly, unreacted starting material was recovered, 1.44 g (32%); and subsequently, the required product 2-(2-chloro-3-phenoxyphenyl)-4,4-dimethyl-4,5-dihydrooxazole 2.81 g (55%), was obtained as a viscous gum.

c) 2-(2-Chloro-3-phenoxyphenyl)-4,4-dimethyl-4,5-dihydrooxazole (2.80 g, 9.28 mmol) was heated with methyl iodide (1.8 mL) in nitromethane (4.0 mL) for 24 hr, (bath temp ca 70° C.). The brown solution was allowed to cool and $Et_2O$ was added until a slight cloudiness was observed. Crystallization commenced almost immediately and the mixture was allowed to stand in the freezer overnight. Large off-white crystals of the product: 2-(2-chloro-3-phenoxyphenyl)-3,4,4-trimethyl-4,5-dihydrooxazolium iodide were obtained. 3.51 g, (85%).

d) The quaternary iodide (3.48 g, 7.83 mmol) was stirred in EtOH (34 mL), and sodium borohydride (1.07 g, 28.28 mmol) was added portionwise, over ca 1 hr. After stirring for a further 1 hr, HCl (2M; 36 mL) was added with care. This mixture was stirred for 1 hr, and after saturating with NaCl, was extracted with $Et_2O$ (2×). The combined (brownish) extracts were washed with aq. $Na_2S_2O_3$, water and then saturated aqueous NaCl; dried ($MgSO_4$) and evaporated to a gum. This was dissolved in THF (30 mL) and 5M HCl was added to the point of cloudiness. The mixture was refluxed for 30 min. and after cooling, water was added, followed by solid potassium bicarbonate (carefully) until effervescence ceased. The THF was then removed in vacuo, NaCl added and the mixture extracted with $Et_2O$ (2×). The combined extracts were washed with $H_2O$ and then saturated aqueous NaCl, dried ($MgSO_4$) and evaporated to give, as a virtually colourless crystalline solid: 2-chloro-3-phenoxybenzaldehyde, 1.35 g (74%).

From this point on the synthesis follows the route described above for Example 3.

e) Sodium ethoxide was prepared from sodium metal (0.50 g, 21.75 mmol) in EtOH (18 mL) and after cooling, a mixture of ethyl azidoacetate (2.88 g, 22.31 mmol) and 2-chloro-3-phenoxybenzaldehyde (1.28 g, 5.47 mmol) was added. After 1.5 hr the reaction was worked-up, and chromatography (silica gel; hexane/$Et_2O$; 0–10%) gave the product: ethyl 2-azido-3-(2-chloro-3-phenoxy phenyl) propenoate as a yellow oil, 0.913 g (49%).

f) The azide (0.904 g, 2.63 mmol) in xylene (42 mL) was added to refluxing xylene (49 mL) under an atmosphere of $N_2$. After refluxing for 1 hr the solution was cooled and evaporated, and the residue was chromatographed (silica gel; hexane/$Et_2O$) to give the product: ethyl 4-chloro-5-phenoxyindole-2-carboxylate; small very pale yellow crystals from hexane/toluene, 0.313 g (37%).

g) Ethyl 4-chloro-5-phenoxyindole-2-carboxylate (0.302 g, 0.956 mmol) was hydrolysed in methanolic NaOH (3.2M, 1.7 mL) at reflux, for 1.5 hr After work-up, the product: 4-chloro-5-phenoxyindole-2-carboxylic acid was obtained as an almost white solid, 0.275 g (ca 100%).

h) The carboxylic acid (0.22 g, 0.765 mmol) was heated (Varitemp heat gun,ca 400° C.) to give a dark oil. This was chromatographed (silica gel; hexane/$Et_2O$) giving 4-chloro-5-phenoxyindole, as a greenish solid, 0.147 g (79%).

i) Treatment of a cooled solution of N,N,N',N'-tetramethyldiaminomethane (0.083 g, 0.11 mL, 0.812 mmol) in $CH_2Cl_2$ (2.4 mL) with acetyl chloride (0.064 g, 0.057 mL, 0.80 mmol) followed by a solution of 4-chloro-5-phenoxy indole (0.14 g, 0.574 mmol) in $CH_2Cl_2$ (2 mL), gave after work-up: 3-(N,N-dimethylaminomethyl)4-chloro-5-phenoxyindole, as an off-white solid. This was treated with potassium cyanide (0.143 g, 2.19 mmol) and methyl iodide (0.0.33 g, 0.143 mL, 2.29 mmol) in DMF (1 mL) for 16 hr After appropriate work-up and chromatography (silica gel; hexane/$Et_2O$; 0–55%), 3-cyanomethyl-4-chloro-5-phenoxyindole was obtained as an off-white crystalline solid, 0.094 g (58%).

j) The cyanomethyl compound (0.09 g, 0.318 mmol) was hydrogenated in MeOH (6 mL) and $Me_2NH$ (6 mL) over Raney nickel, at room temperature and 40 psi. After work-up and treatment with $BOC_2O$ (0.06 g) in $^iPrOH$ (ca 2 mL), for 2 hr, evaporation gave a gum which was chromatographed (silica gel; hexane/$Et_2O$; 0–60% and then $CH_2Cl_2$/EtOH containing 2% concentrated aqueous $NH_3$; 0–15%). The less polar component: 1-(tert-butoxycarbonylamino)-2-(4-chloro-5-phenoxyindol-3-yl)ethane was obtained as a gum, 0.012 g (10%). The more polar component: 1-(N,N-dimethylamino)-2-(4-chloro-5-phenoxyindol-3-yl)ethane, also a gum, 0.035 g, (35%); was treated with oxalic: acid (0.02 g) in MeOH, followed by addition of $Et_2O$, to give: 1-(N,N-dimethylamino)-2-(4-chloro-5-phenoxyindol-3-yl) ethane oxalate, a white crystalline solid, 0.034 g (26%), m.p. 163°–66° C.

EXAMPLE 7

3-(1-Methyl-1,2,5,6-tetrahydropyrid-4-yl)-5-(4-methoxyphenoxy)indole 5-(4-Methoxyphenoxy)indole (as prepared above; 0.411 g, 1.72 mmol) and 1-methyl-piperid-4-one (0.24 mL) were refluxed with sodium methoxide (0.108 g) in MeOH (24 mL) for 16 hr Tlc indicated that reaction was not complete and reflux was therefore continued over a 24 hr period. Over this period further 4-methylpiperidone (4×0.24 mL) and NaOMe (0.108 g) were added. After standing at room temperature for 48 hr, the mixture was diluted with water and the MeOH was evaporated in vacuo. The residual mixture was extracted with EtOAc (3×) and the combined extracts were washed with $H_2O$ and then saturated aqueous NaCl; dried (MgSO4) and evaporated to a yellow solid, which was chromatographed (silica gel; $CH_2Cl_2$/EtOH), giving the product as a pale yellow solid. This was dissolved in MeOH and treated with oxalic acid (0.15 g). On addition of $Et_2O$, yellow needles were obtained of: 3-(1-methyl-1,2, 5,6-tetrahydropyrid-4-yl)-5-(4-methoxyphenoxy)indole oxalate, 0.283 g (39%), m.p. 157°–65° C. decomp.

EXAMPLE 8

3-(1-Methyl-1,2,5,6-tetrahydropyrid-4-yl)-5-phenoxyindole

5-Phenoxyindole (0.30 g, 1.43 mmol), 1-methylpiperid-4-one (0.188 g, 0.2 mL, 1.66 mmol) and sodium methoxide (0.09 g) were heated at reflux in MeOH (20 mL) for 20 hr. After cooling, water was added and most of the MeOH was evaporated in vacuo. The residual mixture was diluted with water, extracted with EtOAc (2×) and the combined extracts were washed with water, dried (MgSO$_4$) and evaporated to give: 3-(1-methyl-1,2,5,6-tetrahydropyrid-4-yl)-5-phenoxyindole, a yellow solid 0.243 g, (56%). The free base (0.1 g) was dissolved in MeOH and treated with fumaric acid (0.057 g, 0.49 mmol). Et$_2$O was added to the point of cloudiness and the mixture was kept at ca 4° C. for 48 hr, to afford: 3-(1-methyl-1,2,5,6-tetrahydropyrid-4-yl)-5-phenoxyindole fumarate, a pale yellow crystalline solid, 0.072 g (52%), m.p. 135°–37° C.

EXAMPLE 9

3-(1-Methyl-1,2,5,6-tetrahydropyrid-4-yl)-5-phenylthioindole

This preparation was carried out in a similar manner to that of Example 8.

5-Phenylthioindole (0.50 g, 2.22 mmol), 1-methylpiperid-4-one (0.292 g, 0.32 mL, 2.58 mmol) and sodium methoxide (0.139 g) were heated at reflux in MeOH (25 mL) for 20 hr. After cooling and work-up, 3-(1-methyl-1,2,5,6-tetrahydropyrid-4-yl)-5-phenylthioindole was obtained as a pale yellow solid, 0.399 g, (56%). This free base (0.20 g) was treated with fumaric acid (0.11 g, 0.94 mmol) in MeOH/Et$_2$O to give: 3-(1-methyl-1,2,5,6-tetrahydropyrid-4-yl)-5-phenylthioindole fumarate, 0.124 g (46%), m.p. 225°–28° C.

EXAMPLE 10

1-Amino-2-(5-(pyrid-3-yloxy)indol-3-yl)ethane (10A) and 1-(N,N-dimethylamino)-2-(5-(pyrid-3-yloxy)indol-3-yl)ethane (10B)

a) To a solution of 3-hydroxypyridine (15.0 g, 157 mmol) in DMF (60 mL) were added potassium carbonate (15.36 g, 110 mmol) and copper powder (1.2 g). The mixture was stirred under N$_2$ for 15 min. and then a solution of 5-fluoro-2-nitrotoluene (12.29 g, 79 mmol) in DMF (10 mL) was added dropwise over ca 0.5 hr. The mixture was stirred at reflux for 5 hr and then allowed to cool EtOAc was added and the black solid precipitate produced, was removed by filtration and discarded. NaOH aq. (1M, 100 mL) was added, and the two-phase mixture filtered through Hyflo to remove insoluble tarry material. The EtOAc layer was then separated, dried (MgSO$_4$) and evaporated to give a dark oil. Chromatography (silica gel;hexane/EtOAc; 0–24%) gave the product: 2-nitro-5-(pyrid-3-yloxy)toluene, a yellow solid, 8.0 g (22%).

b) 2-Nitro-5-(pyrid-3-yloxy)toluene (6 g, 26 mmol), dimethylformamidedimethyl acetal (5.43 g, 45 mmol) and pyrrolidine (3.24 g, 45 mmol) were heated in DMF (70 mL) at reflux, for 3 hr. The DMF was evaporated in vacuo to leave a deep red oil, which was dissolved in MeOH (200 mL) and the solution cooled in an ice-bath. Raney nickel (3 spatulas) was added, followed by addition of hydrazine hydrate (24 mL; portionwise, to moderate the vigour of the reaction). Once addition was complete, the mixture was stirred for 1 hr at room temp and the Raney nickel residue was then removed by filtration. The filtrate was evaporated and water added to the residue, which was then extracted with EtOAc (2×). The extracts were dried (MgSO$_4$) and evaporated to a gum, which was chromatographed (silica gel; hexane/ EtOAc; 0–42%), giving, as a white solid: 5-(pyrid-3-yloxy) indole, 1.60 g (24%).

From this point the preparation follows closely the corresponding stages of the synthesis of Example 3.

c) Treatment of a cooled solution of N,N,N',N'-tetramethyldiaminomethane (0.829 g, 1.11 mL, 8.12 mmol) in CH$_2$Cl$_2$ (10 mL) with acetyl chloride (0.637 g, 0.573 mL, 8.12 mmol) followed by a solution of 5-(pyrid-3-yloxy) indole (1.23 g, 5.8 mmol) in CH$_2$Cl$_2$ (100 mL), gave after work-up: 3-(N,N-dimethylaminomethyl)-5-(pyrid-3-yloxy) indole as a gum. This was treated with finely ground potassium cyanide (1.246 g, 19 mmol) and methyl iodide (2.7 g, 1.18 mL, 19 mmol) in DMF (70 mL) for 16 hr, and after appropriate work-up and chromatography (silica gel; hexane/EtOAc; 0–60%), 3-cyanomethyl-5-(pyrid-3-yloxy) indole was obtained a gum, which solidified on standing, 0.655 g (45%).

d) The cyanomethyl compound (0.655 g, 2.6 mmol) was hydrogenated in MeOH (100 mL) and Me$_2$NH (20 mL) over Raney nickel, at room temperature and 50 psi. After work-up and treatment with BOC$_2$O (excess) in $^i$PrOH, evaporation gave a gum which was chromatographed (silica gel; hexane/ Et$_2$O; 0–100% and then CH$_2$Cl$_2$/EtOH containing 2% concentrated aqueous NH$_3$; 0–15%). Two products were obtained: (i) 1-tert-butoxycarbonylamino-2-(5-(pyrid-3-yloxy)indol-3-yl)ethane, a colourless gum, 0.10 g (11%) and (ii) 1-(N,N-dimethylamino)-2-(5-(pyrid-3-yloxy) indol-3-yl)ethane; a gum, 0.20 g (27%). Treatment of the less polar compound with HCl/Et$_2$O in MeOH gave, as light brown hygroscopic solid: 1-amino-2-(5-(pyrid-3-yloxy)indol-3-yl) ethane hydrochloride (10A). The more polar column fraction on treatment with oxalic acid in MeOH, followed by addition of Et$_2$O, gave: 1-(N,N-dimethylamino)-2-(5-(pyrid-3-yloxy)indol-3-yl)ethane oxalate (10B), m.p 178°–80° C.

EXAMPLE 11

1-Amino-2-(5-(pyrimidin-2-yloxy)indol-3-yl)ethane (11A) and 1-(N,N-dimethylamino)-2-(5-(pyrimidin-2-yloxy)indol-3-yl)ethane (11B)

a) A mixture of 5-hydroxyindole (2.50 g, 18.7 mmol), 2-chloropyrimidine (4.3 g, 37.6 mmol) and powdered KOH (1.049 g, 18.7 mmol) was warmed in DMSO (50 mL) at 40° C. for 5 hr, under an atmosphere of N$_2$. The dark solution was cooled and poured into saturated aqueous NaCl and the mixture was extracted with EtOAc (3×). The extracts were dried and evaporated, and the residue was chromatographed (silica gel; hexane/EtOAc; 0–70%),giving, as a white solid: 5-(pyrimidin-2-yloxy)indole, 1.12 g (28%).

From this point the preparation follows closely the corresponding stages of the synthesis of Example 3.

b) Treatment of a cooled solution of N,N,N',N'-tetramethyldiaminomethane (0.854 g, 1.14 mL, 8.36 mmol) in CH$_2$Cl$_2$ (10 mL) with acetyl chloride (0.657 g, 0.59 mL, 8.36 mmol) followed by a solution of 5-(pyrimidin-2-yloxy) indole (1.268 g, 6.00 mmol) in CH$_2$Cl$_2$ (110 mL), gave after work-up: 3-(N,N-dimethylaminomethyl)-5-(pyrimidin-2-yloxy)indole as a yellow solid. This was treated with finely ground potassium cyanide (1.37 g, 21 mmol) and methyl iodide (2.94 g, 1.28 mL, 21 mmol) in DMF (70 mL) for 16 hr, and after appropriate work-up, 3-cyanomethyl-5-(pyrimidin-2-yloxy)indole was obtained as a light yellow solid, 0.98 g (65%).

c) The cyanomethyl compound (0.98 g, 3.9 mmol) was hydrogenated in MeOH (150 mL) and Me$_2$NH (20 mL) for 1 hr, over Raney nickel, at room temperature and 50 psi. After removal of the catalyst by filtration, evaporation gave a gum which was chromatographed (silica gel; CH$_2$Cl$_2$/MeOH containing 10% concentrated aqueous NH$_3$; 0–10%). Two products were obtained: (i) 1-(N,N-dimethylamino)-2-(5-(pyrimidin-2-yloxy)indol-3-yl)ethane, a gum, 0.32 g (29%) and (ii) 1-amino-2-(5-(pyrimidin-2-yloxy)indol-3-yl) ethane, also a gum, 0.072 g (7%). Both free bases were converted into their respective oxalate salts by treatment with oxalic acid in MeOH/Et$_2$O. The former amine gave: 1-N,N-dimethylamino-2-(5-(pyrimidin-2-yloxy)indol-3-yl) ethane oxalate (11A), a white crystalline solid, m.p. 174°–76° C. The more polar amine gave: 1-amino-2-(5-(pyrimidin-2-yloxy)indol-3-yl)ethane oxalate (11B), an off-white solid m.p. 178°–80°.

EXAMPLE 12

3-(1-Methyl-1,2,5,6-tetrahydropyrid-4-yl)-5-(pyrid-2-yloxy)indole a) 2-Hydroxypyridine (5 g, 52 mmol), 5-fluoro-2-nitrotoluene (4.09 g, 26.4 mmol), potassium carbonate (7.26 g, 52 mmol) and copper powder (0.5 g) were heated together in DMF (10 mL), at reflux for 5 hr. After cooling, EtOAc was added and the resulting black solid precipitate was removed by filtration and discarded. The filtrate was washed with aq. NaOH (1M; 3×), dried (MgSO$_4$) and evaporated to give a dark yellow solid. This was chromatographed (silica gel; hexane/EtOAc; 0–100% and then EtOAc/MeOH; 0–5%) giving: 2-nitro-5-(pyrid-2-yloxy)toluene, a light yellow solid, 1.50 g (12% ).

b) 2-Nitro-5-(pyrid-2-yloxy)toluene (1.11 g, 4.82 mmol), dimethylformamide dimethylacetal (1.018 g, 8.54 mmol) and pyrrolidine (0.6 g, 84.36 mmol) were heated in DMF (25 mL) at reflux, for 3 hr. The DMF was evaporated in vacuo to leave a deep red oil, which was dissolved in MeOH (80 mL) and the solution cooled in an ice-bath. Raney nickel (2 spatulas) was added, followed by addition of hydrazine hydrate (4 mL; portionwise, to moderate the vigour of the reaction). Once addition was complete, the mixture was stirred for 1.5 hr at room temp and the Raney nickel residue was then removed by filtration (Hyflo). The filtrate was evaporated and water added to the residue giving a brown solid, which was collected by filtration and chromatographed (silica gel; hexane/EtOAc; 0–100% and then EtOAc/MeOH 0–3%) to afford, as a light yellow solid: 5-(pyrid-2-yloxy)indole, 0.22 g (23%).

The remaining stage of this preparation was carried out in a similar manner to that of Example 8.

c) 5-(Pyrid-2-yloxy)indole (0.22 g, 1.04 mmol), 1-methylpiperid-4-one (0.235 g, 2.08 mmol) and sodium methoxide (0.337 g) were heated at reflux in MeOH (20 mL) for 48 hr, over activated molecular sieves. After cooling and work-up, the residue was chromatographed (silica gel; CH$_2$Cl$_2$/MeOH; 0–25%) to give 3-(1-methyl-1,2,5,6-tetrahydropyrid-4-yl)-5-(pyrid-2-yloxy)indole, a gum, 0.083 g (26%). This free base was treated with oxalic acid in MeOH/Et$_2$O to give: 3-(1-methyl-1,2,5,6-tetrahydropyrid-4-yl)-5-(pyrid-2-yloxy)indole oxalate, m.p. 240°–45° C.

EXAMPLE 13

1-(N,N-Dimethylamino)-2-(5-(4-bromophenoxy)indol-3-yl)ethane

This preparation was carried out by adaptation of those of Examples 3 and 8.

a) Phenol (73.02 g, 780 mmol), 5-fluoro-2-nitrotoluene (60.18 g, 390 mmol), potassium carbonate (75.02 g, 540 mmol) and copper powder (3.0 g) were heated together in DMF (150 mL), at reflux for 16 hr. After cooling and work-up, the dark material so obtained, was chromatographed (silica gel; hexane/Et$_2$O; 0–3%), giving: 2-nitro-5-phenoxytoluene, an orange oil, 72.42 g (81%).

b) 5-Phenoxy-2-nitrotoluene (2.0 g, 8.72 mmol) and N-bromosuccinimide (2.33 g, 13.09 mmol) were stirred at 70° C. in DMF (30 mL) over a period of 64 hr. Over this period additional NBS (total 1.87 g, 10.48 mmol) was added in four portions. The mixture was cooled and then partitioned between H$_2$O/EtOAc. The organic extract was washed (H$_2$O), dried (MgSO$_4$) and evaporated to give: 5-(4-bromophenoxy)-2-nitrotoluene as a yellow oil, (2.86 g) slightly contaminated with starting material, but sufficiently pure to be carried through to the next stage.

c) 5-(4-Bromophenoxy)-2-nitrotoluene (3.12 g), dimethylformamidediethyl acetal (1.77 g, 2.1 mL, 12.02 mmol) and pyrrolidine (0.863 g, 1.01 mL, 12.13 mmol) were heated in DMF (30 mL) at 120° C. for 2 hr. The DMF was evaporated in vacuo to leave a deep red. oil. This was dissolved in MeOH (30 mL), and after cooling, Raney nickel (1 spatula) was added, followed by addition of hydrazine hydrate (1.8 mL; portionwise). After ca 1 hr the Raney nickel was removed by filtration and the filtrate evaporated. The residue was worked-up (Et$_2$O/sat.aq.NaCl) and chromatographed (silica gel; hexane/EtOAc; 0–10%) to afford, as a greenish solid: 5-(4-bromophenoxy)indole, 0.394 g (ca 13%; containing trace contaminants)

d) Treatment of a cooled solution of N,N,N',N'-tetramethyldiaminomethane (0.186 g, 0.25 mL, 1.83 mmol) in CH$_2$Cl$_2$ (10 mL) with acetyl chloride (0.143 g, 0.13 mL, 1.83 mmol) followed by a solution of 5-(4-bromophenoxy) indole (0.394 g, 1.37 mmol) in CH$_2$Cl$_2$ (5 mL), gave after work-up 2-(N,N-dimethylaminomethyl)-5-(4-bromophenoxy)indole as a brown gum. This was treated with finely ground potassium cyanide (0.34 g, 5.21 mmol) and methyl iodide (0.77 g, 0.34 mL, 5.44 mmol) in DMF (30 mL) for 16 hr, and after appropriate work-up, 3-cyanomethyl-5-(4-bromophenoxy)indole was obtained as a brown gum 0.29 g, (ca 65%; carried through to next stage without further purification).

e) The cyanomethyl compound (0.29 g) was hydrogenated for 1 hr in MeOH (20 mL) and Me$_2$NH (15 mL) over Raney nickel, at room temperature and 40 psi. After work-up and treatment with BOC$_2$O (excess) in $^i$PrOH, evaporation gave a gum which was chromatographed (silica gel; CH$_2$Cl$_2$/MeOH; 0–20%). The less polar component was not obtained pure and was discarded. The more polar component: 1-(N,N-dimethylamino)-2-(5-(4-bromophenoxy) indol-3-yl)ethane was obtained as a gum, 0.084 g (ca 25%). Further purification was effected by prep. hplc, and the resulting material was treated with oxalic acid (0.012 g, 0.092 mmol) in MeOH/Et$_2$O to give: 1-(N,N-dimethylamino)-2-(5(4-bromophenoxy)indol-3-yl)ethane oxalate, an off-white solid, 0.01 g (2%), m.p. 160°–62°.

EXAMPLE 14

1-(N,N-Dimethylamino)-2-(5-(4-methoxypyrimidin-2-yloxy) indol-3-yl)ethane

This preparation was carried out in a similar manner to that described above for Example 11.

a) 5-Hydroxyindole (8.6 g, 64 mmol), 2-chloro-6-methoxypyrimidine (9.9 g, 68 mmol) and powdered KOH (3.59 g, 64 mmol) were heated together in DMSO (70 mL) at 80° C. for 5 hr. After cooling and work-up, chromatography (hexane/EtOAc; 0–27%) gave: 5-(4-methoxypyrimidin-2-yl)indole, 3.0 g, (18%).

b) Treatment of a cooled solution of N,N,N',N'-tetramethyldiaminomethane (1.18 g, 1.58 mL, 11.5 mmol) in $CH_2Cl_2$ (10 mL) with acetyl chloride (0.90 g, 0.81 mL, 11.5 mmol) followed by a solution of 5-(4-methoxypyrimidin-2-yloxy)indole (2.0 g, 8.2 mmol) in $CH_2Cl_2$ (100 mL), gave after work-up: 3-(N,N-dimethylaminomethyl)-5-(4-methoxypyrimidin-2-yloxy)indole as a white solid. This was treated with finely ground potassium cyanide (1.75 g, 26.8 mmol) and methyl iodide (3.80 g, 1.65 mL, 26.8 mmol) in DMF (130 mL) for 16 hr, and after appropriate work-up, 3-cyanomethyl-5-(4-methoxypyrimidin-2-yloxy)indole was obtained as a white solid, 2.20 g (96%).

c) The cyanomethyl compound (2.20 g, 7.8 mmol) was hydrogenated in MeOH (200 mL) and $Me_2NH$ (30 mL) for 2 hr over Raney nickel; at room temperature and 50 psi. After removal of the catalyst by filtration, evaporation gave a solid residue (1.8 g) which was treated with $BOC_2O$ (2.2 g, ca 10 mmol) in DMF (60 mL), at room temperature for 4 hr. Work-up (EtOAc/$H_2O$) followed by chromatography (silica gel; hexane/EtOAc; 0–50% and then $CH_2Cl_2$/MeOH; 0–40%) gave two products:

(i) 1-tert-butoxycarbonylamino-2-(5-(4-methoxypyrimidin-2-yloxy)indol-3-yl)ethane, a white solid, 0.23 g (8%) and (ii) 1-(N,N-dimethylamino)-2-(5-(4-methoxypyrimidin-2-yloxy)indol-3-yl)ethane, a gum, 0.08 g (3%). The latter product was treated with oxalic acid in MeOH/$Et_2$o to give: 1-(N,N-dimethylamino)-2-(5-(4-methoxypyrimidin-2-yloxy)indol-3-yl)ethane oxalate, a white solid, m.p. 203°–04° C. The less polar (tBOC) product of the hydrogenation was unstable in the presence of acid.

EXAMPLE 15

3-(1-Methyl-1,2,5,6-tetrahydropyrid-4-yl)-5-(pyrid-2-ylthio)indole a) 5-Bromo-1-triisopropylsilylindole (5.0 g, 14.19 mmol) was dissolved in THF (dry; 60 mL) and, under an atmosphere of dry $N_2$, the solution was cooled to –65° C. tert-Butyllithium solution (1.7M in pentane; 30 mL, 50.37 mmol) was added over ca 0.5 hr to give a yellow solution which was stirred at –65° C. for a further 1 hr. A solution of 2,2'-dipyridyldisulphide (15.72 g, 71.37 mmol) in THF (30 mL) was then added over a period of 20 min. and after a further 20 min at –65° C., the mixture was allowed to warm slowly to room temperature and stirred for ca 16 hr. Tetra-n-butylammonium fluoride solution (1.0M in THF; 30 mL) was added, and after stirring at room temperature for 3 hr, sainted aqueous NaCl was added and the mixture extracted with $Et_2O$. The ethereal layer was washed with saturated aqueous NaCl, dried ($MgSO_4$) and evaporated in vacuo. The residue was chromatographed (silica gel; hexane/$Et_2O$; 0–40%) to afford: 5-(pyrid-2-ylthio)indole, as a cream coloured solid, 1.98 g (62%).

The final stage of this preparation was carried out in a similar manner to that of Example 8.

b) 5-(Pyrid-2-ylthio)indole (0.347 g, 1.53 mmol), 1-methylpiperid-4-one (0.347 g, 0.38 mL, 3.06 mmol), sodium methoxide (0.497 g) and some finely ground molecular sieves were heated in refluxing MeOH (20 mL) for 24 hr. After work-up and chromatography (silica gel; $CH_2Cl_2$/MeOH; 0–15%), 3-(1-methyl-1,2,5,6-tetrahydropyrid-4-yl)-5-(pyrid-2-ylthio)indole was obtained as a yellow solid (0.35 g). This was treated with fumaric acid (0.189 g, 1.6 mmol) in MeOH/$Et_2O$ to give, as a pale yellow crystalline solid: 3-(1-methyl-1,2,5,6-tetrahydropyrid-4-yl)-5-(pyrid-2-ylthio)indole fumarate, 0.227 g (34%), m.p. 226°–28° C.

EXAMPLE 16

1-(N,N-Dimethylamino)-2-(5-benzylindol-3-yl)ethane a) 5-Bromo-1-triisopropylsilylindole (2.0 g, 5.68 mmol) was dissolved in THF (dry, 30 mL) and the solution cooled to –70° C. tert-Butyllithium (1.7M in hexane; 10.7 mL, 18.2 mmol) was added, and by the time addition was complete, a permanent yellow coloration had been produced. After a further 1 hr at –65° C. benzaldehyde (0.658 g, 6.20 mmol) was added and the mixture stirred at ca –65° C. for 1 hr before warming gradually to room temperature $H_2O$ and NaCl were added to the mixture which was then extracted (3×) with $Et_2O$, and the extracts were combined, washed ($H_2O$, 3× and then saturated aqueous NaCl) and dried ($MgSO_4$). Evaporation gave a gum which was chromatographed (silica gel; hexane/$Et_2O$; 0–30%). Recovered starting material, 0.437 g (22%) eluted first; followed by the product: phenyl(1-triisopropylsilylindol-5-yl)methanol, a gum which solidified on standing, 0.61 g (28%; several fractions containing contaminated product were subsequently obtained). The pure product (0.6 g, 1.58 mmol) was dissolved in THF (10 mL) and treated with tetra-n-butylammonium fluoride solution (1.0M in THF; 3.0 mL) at room temperature. The mixture was stirred for 1.5 hr and then partitioned between $Et_2O$ and saturated aqueous NaCl. After re-extracting the aqueous layer ($Et_2O$; 2×), the combined ethereal layers were washed with saturated aqueous NaCl, dried ($MgSO_4$) and evaporated to a gum which was chromatographed (silica gel; hexane/$Et_2O$; 0–50%), giving: phenyl(indol-5-yl)methanol, as an almost colourless gum, 0.347 g (98%). This material was hydrogenated in EtOH (25 mL) over Pd-C (5%; a total of 0.30 g was added over the reaction period, in two portions), at 45 psi, for ca 40 hr. The catalyst was filtered off, and the filtrate evaporated to a gum which was chromatographed (silica gel; hexane/$Et_2O$; 0–50%). The required product: 5-benzylindole, was obtained as an off white solid, 0.135 g (44%), as well as 5-benzylindoline 0.03 g, (10%) and unreacted starting material, 0.013 g (4%).

b) 5-Benzylindole (0.563 g, 2.716 mmol) was dissolved in dry $Et_2O$ (8 mL) and the solution cooled in an ice-bath. A solution of oxalyl chloride (0.47 g, 0.32 mL, 3.67 mmol) in dry $Et_2O$ (6 mL) was added over ca 15 min. An orange precipitate was observed and after standing at ca 4° C. for 16 hr, this solid was collected by filtration, and blown dry with a current of dry $N_2$. This acid chloride was immediately suspended in dry $CH_2Cl_2$ (35 mL), and while cooling (ice-bath) and stirring, a solution of $Me_2NH$ in $Et_2O$ was added (1.6M; 4.5 mL; freshly prepared) over 5 min. The starting material dissolved to give a very pale yellow solution which was stirred at ice-bath temperature for 1 hr and then allowed to warm to room temperature. This solution was then diluted with $CH_2Cl_2$, washed successively with aq. $K_2CO_3$, $H_2O$ and saturated aqueous NaCl, and dried ($MgSO_4$). Evaporation gave a solid which was triturated with $Et_2O$ to afford as a white powder: 3-(N,N-dimethylglyoxamido)-5-benzylindole, 0.604 g (90%).

c) A solution of $AlH_3$ was prepared by addition of c.$H_2SO_4$ (1.59 g) dropwise to a cooled (ice-bath) suspension of $LiAlH_4$ (1.226 g) in dry THF (82 mL) over 20 min. The mixture was them left to stand under dry $N_2$ for 1 hr to allow the solids to settle. A solution of the glyoxamide (0.59 g, 1.926 mmol) in THF (110 mL) was prepared, and in a $N_2$ atmosphere, the $AlH_3$ solution (55 mL) was added over 5 min. The mixture was stirred for 16 hr and then $H_2O$ was added dropwise to quench excess reagent, and the THF was evaporated in vacuo. The residue was partitioned between 1M $HCl/CH_2Cl_{12}$ and after re-extraction of the aqueous layer (2×; $CH_2Cl_2$), the combined organic layers were washed with 1M HCl and then saturated aqueous NaCl, dried ($MgSO_4$) and evaporated to a solid. Chromatography (silica gel; $CH_2Cl_2$/EtOH containing 2% concentrated aqueous $NH_3$; 0–12%), gave the free base: 1-(N,N-dimethylamino)-2-(5-benzylindol-3-yl)ethane, as a gum, 0.246 g (46%). This was treated with oxalic acid (0.07 g) in MeOH (2 mL) and $Et_2O$ added until crystallisation commenced. The product: 1-(N,N-dimethylamino)-2-(5-benzylindol-3-yl)ethane oxalate, was obtained as white granular crystals, 0.191 g (27%), m.p.158°–9° C.

Pharmaceutical formulations

EXAMPLE A

A tablet for oral administration is prepared by combining

|  | Mg/Tablet |
|---|---|
| Compound of formula (I) | 100 |
| lactose 153 | |
| starch 33 | |
| crospovidone | 12 |
| microcrystalline cellulose | 30 |
| magnesium stearate | 2 |
| | 330 mg | into a 9 mm tablet.

EXAMPLE B

An injection for parenteral administration is prepared from the following

|  | % w:w |
|---|---|
| Compound of formula (I) | 0.50% (w:v) |
| 1M citric acid | 30% (v:v) |
| sodium hydroxide (qs) | to pH 3.2 |
| water for injection BP | to 100 ml |

The compound of formula (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

We claim:

1. A compound of structure (I):

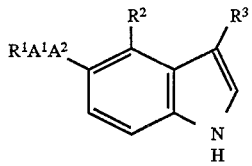

Structure (I)

in which
$A^1$ is O, $S(O)_n$ in which n is 0,1 or 2, NR, $CH_2$, or CH(OH);
$A^2$ is a bond or $CH_2$; or
$A^1A^2$ is CH=CH;
R is hydrogen or $C_{1-4}$alkyl;

$R^1$ is a 6- to 10-membered aryl or heteroaryl ring, optionally substituted by up to 3 groups selected from halo, $C_{1-4}$alkyl, hydroxy, oxo, $C_{1-4}$alkoxy, $—CO_2R^9$, $—NHCOR^9$, $—CONR^{10}R^{11}$, $—SO_2NR^{10}R^{11}$, $—NHSO_2R^{12}$, $NO_2$, $—NR^{10}R^{11}$, $—NHCONH_2$, CN, $CF_3$, or $CF_3O$, wherein $R^9$ to $R^{11}$ are independently hydrogen or $C_{1-4}$alkyl and $R^{12}$ is $C_{1-4}$alkyl;
$R^2$ is hydrogen, halogen, $C_{1-4}$alkyl, CN, $NO_2$ or $CF_3$;
$R^3$ is $C(R^4)(R^5)CH_2NR^6R^7$, $—CH=NNHC(NH)NH_2$ or

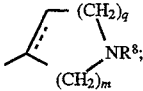

$R^4$ and $R^5$ are independently hydrogen or $C_{1-4}$alkyl;
$R^6$ and $R^7$ are the same or different and are each hydrogen or $_{1-4}$alkyl or together with the nitrogen atom to which they are attached form a ring;
$R^8$ is hydrogen, $C_{1-4}$alkyl, or $C_{3-6}$alkenyl;
the dotted lines represent an optional bond; and
q and m are independently 1 or 2;
and pharmaceutically acceptable salts, solvates and hydrates thereof, with the proviso that $R^1$ is not a 6- to 10-membered aryl or heteroaryl ring optionally substituted by up to 3 groups selected from halo, $C_{1-4}$alkyl, $CO_2R^9$, $NHCOR^9$, $CONR^{10}R^{11}$, $SO_2NR^{10}R^{11}$, $NHSO_2R^{12}$, $NO_2$, $NR^{10}R^{11}$, $NHCONH_2$ or CN, when $A^1A^2$ is O, S or NH, $R^2$ is hydrogen and
$R^3$ is $(CH_2)_2NR^6R^7$ or

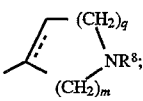

and with the further proviso that $R^1$ is not 3-$CF_3$-2-pyridyl, when $A^1A^2$ is NH, $R^2$ is hydrogen and $R^3$ is $CH_2CH_2NMe_2$.

2. A compound according to claim 1 where $A^1$ is O, S, NR or $CH_2$ and $A^2$ is a bond or $CH_2$.

3. A compound according to claim 1 where $R^1$ is optionally substituted phenyl or naphthyl.

4. A compound according to claim 1 wherein $R^1$ is an optionally substituted 6- to 10-membered heteroaryl ring containing from 1 to 4 nitrogen atoms.

5. A compound according to claim 1 wherein $R^2$ is hydrogen or halogen.

6. A compound according to claim 1 wherein $R^3$ is $—CH=NNHC(NH)NH_2$ or $C(R^4)(R^5)CH_2NR^6R^7$ and $R^4$ and $R^5$ are both hydrogen or methyl.

7. A compound according to any claim 1 wherein $R^6$ and $R^7$ are both hydrogen or methyl.

8. A compound according to claim 1 where $R^3$ is a group

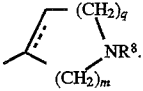

9. A compound of structure (I) according to claim 1:
3-(2-N,N-dimethylaminoethyl)-5-phenoxyindole,
3-(2-N,N-dimethylaminoethyl)-5-phenylthioindole,
1-amino-2-(5-(4-methoxyphenoxy)indol-3-yl)ethane,
1-(N,N-dimethylamino)-2-(5-(4-methoxyphenoxy)indol-3-yl)ethane,
1-amino-2-(5-(4-methylphenoxy)indol-3-yl)ethane,
1-(N,N-dimethylamino)-2-(5-(4-methylphenoxy)indol-3-yl)ethane, 1-amino-2-(5-(3-trifluoromethylphenoxy)indol-3-yl)ethane,
1-(N,N-dimethylamino)-2-(5-(3-trifluoromethylphenoxy)indol-3-yl)ethane,
1-(N,N-dimethylamino)-2-(4-chloro-5-phenoxyindol-3-yl)ethane,
3-(1-methyl-1,2,5,6-tetrahydropyrid-4-yl)-5-(4-methoxyphenoxy)indole,
3-(1-methyl-1,2,5,6-tetrahydropyrid-4-yl)-5-phenoxyindole,
3-(1-methyl-1,2,5,6-tetrahydropyrid-4-yl)-5-phenylthioindole,
1-amino-2-(5-(pyrid-3-yloxy)indol-3-yl)ethane,
1-(N,N-dimethylamino)-2-(5-(pyrid-3-yloxy)indol-3-yl)ethane,
1-amino-2-(5-(pyrimidin-2-yloxy)indol-3-yl)ethane,
1-(N,N-dimethylamino)-2-(5-(pyrimidin-2-yloxy)indol-3-yl)ethane,
3-(1-methyl-1,2,5,6-tetrahydropyrid-4-yl)-5-(pyrid-2-yloxy)indole,
1-(N,N-dimethylamino)-2-(5-(4-bromophenoxy)indol-3-yl)ethane,
1-(N,N-dimethylamino)-2-(5-(4-methoxypyrimidin-2-yloxy)indol-3-yl)ethane,
3-(1-methyl-1,2,5,6-tetrahydropyrid-4-yl)-5-(pyrid-2-ylthio)indole,
1-(N,N-dimethylamino)-2-(5-benzylindol-3-yl)ethane, or
4-chloro-3-(2-N,N-dimethylaminoethyl)-5-phenylthioindole, or a pharmaceutically acceptable salt, solvate or hydrate thereof.

10. A pharmaceutical composition comprising a compound of structure (I) as defined in claim 1 or a pharmaceutically acceptable salt, solvate or hydrate thereof and a pharmaceutically acceptable carrier.

11. A method of treatment of a condition which requires modulation of the 5-$HT_1$-like receptor which comprises administering to a subject in need thereof an effective amount of a compound of structure (I) as defined in claim 1 or a pharmaceutically acceptable salt, solvate or hydrate thereof.

* * * * *